(12) United States Patent
Dupont et al.

(10) Patent No.: US 12,274,413 B2
(45) Date of Patent: Apr. 15, 2025

(54) AUTONOMOUS ROBOTIC CATHETER FOR MINIMALLY INVASIVE INTERVENTIONS

(71) Applicant: Children's Medical Center Corporation, Boston, MA (US)

(72) Inventors: Pierre E. Dupont, Boston, MA (US); Georgios Fagogenis, Athens (GR); Benoit Rosa, Sarrebourg (FR); Margherita Mencattelli, Brooklyn, NY (US); Zurab Machaidze, Lexington, MA (US)

(73) Assignee: Children's Medical Center Corporation, Boston, MA (US)

( * ) Notice: Subject to any disclaimer, the term of this patent is extended or adjusted under 35 U.S.C. 154(b) by 1028 days.

(21) Appl. No.: 17/154,486

(22) Filed: Jan. 21, 2021

(65) Prior Publication Data

US 2021/0236773 A1      Aug. 5, 2021

Related U.S. Application Data

(60) Provisional application No. 62/965,554, filed on Jan. 24, 2020.

(51) Int. Cl.
*A61B 1/00*      (2006.01)
*A61M 25/01*     (2006.01)

(52) U.S. Cl.
CPC .... *A61B 1/00006* (2013.01); *A61B 1/000094* (2022.02); *A61B 1/000096* (2022.02); *A61B 1/00097* (2022.02); *A61M 25/0116* (2013.01); *A61M 2205/332* (2013.01); *A61M 2205/3327* (2013.01); *A61M 2205/583* (2013.01)

(58) Field of Classification Search
None
See application file for complete search history.

(56) References Cited

U.S. PATENT DOCUMENTS 4,470,407 A * 9/1984 Hussein ............ A61B 1/00165
                                                  600/116
6,132,368 A   10/2000 Cooper
(Continued)

OTHER PUBLICATIONS

Cappabianca et al., "Application of Neuroendoscopy to Intraventricular Lesions," Neurosurgery, Feb. 2008 Supplement, vol. 62, No. 2, pp. SHC575-SHC598.
(Continued)

*Primary Examiner* — John P Leubecker
(74) *Attorney, Agent, or Firm* — Greenberg Traurig, LLP; Melissa Hunter-Ensor; Joshua I. Rudawitz

(57) ABSTRACT

A robotic system comprising a robotic catheter steerable by a motorized drive system, an imaging device positioned on a distal end of the robotic catheter, and a controller configured to: process one or more images captured by the imaging device to identify an anatomical feature, implanted device, or medical instrument; estimate a location of the imaging device in the body based on the identified anatomical feature, implanted device, or medical instrument; determine, based on the estimated location of the imaging device, a direction in which to steer the robotic catheter for advancement towards an interventional site; and monitor at least one of (i) a stream of images captured by the imaging device and (ii) a force or distance measurement captured by the imaging device or a sensor proximate the imaging device, to adjust the direction in which to steer the robotic catheter during advancement towards the interventional site.

31 Claims, 17 Drawing Sheets

(56) References Cited

U.S. PATENT DOCUMENTS

| | | | |
|---|---|---|---|
| 6,866,671 | B2 | 3/2005 | Tierney et al. |
| 7,883,475 | B2 | 2/2011 | Dupont et al. |
| 8,206,406 | B2 | 6/2012 | Orban, III |
| 9,060,678 | B2 | 6/2015 | Larkin et al. |
| 9,457,168 | B2 | 10/2016 | Moll et al. |
| 10,238,457 | B2 | 3/2019 | Herrell et al. |
| 10,307,214 | B2 | 6/2019 | Lathrop et al. |
| 2015/0313446 | A1* | 11/2015 | Ogawa ............... A61B 1/00009 600/117 |
| 2016/0367120 | A1 | 12/2016 | Dupont et al. |
| 2017/0095299 | A1 | 4/2017 | Hendrick et al. |
| 2018/0132699 | A1* | 5/2018 | Inoue ............... A61B 1/00042 |
| 2018/0296281 | A1* | 10/2018 | Yeung ............... A61B 34/32 |
| 2019/0365489 | A1* | 12/2019 | Kasai ............... A61B 1/055 |
| 2021/0052140 | A1* | 2/2021 | Tata ............... A61B 5/067 |
| 2021/0220594 | A1* | 7/2021 | Biro ............... A61B 1/0052 |
| 2021/0228296 | A1 | 7/2021 | Dupont et al. |

OTHER PUBLICATIONS

Da Vinci Surgical System User Manual, 2014, 100 pages.

Dupont et al., "Design and Control of Concentric-Tube Robots," IEEE Transactions on Robotics, Apr. 2010, vol. 26, No. 2, pp. 209-225.

Fagogenis et al., "Autonomous robotic intracardiac catheter navigation using haptic vision," Science Robotics, Apr. 24, 2019, vol. 4, eaaw1977, pp. 1-12.

Fukushima et al., "Endoscopic Biopsy of Intraventricular Tumors with the Use of a Ventriculofiberscope," Neurosurgery, 1978, vol. 2, No. 2, pp. 110-113.

Gaab et al., "Neuroendoscopic approach to intraventricular lesions," Journal of Neurosurgery, Mar. 1998, vol. 88, pp. 496-505.

Hendrick, Richard J., "System Design and Elastic Stability Modeling of Transendoscopic Continuum Robots," Doctoral Dissertation, May 2017, 243 pages.

Lee et al., "Anisotropic Patterning to Reduce Instability of Concentric-Tube Robots," IEEE Transactions on Robotics, Dec. 2015, vol. 31, No. 6, pp. 1311-1323.

Luo et al., "Designing Concentric Tube Manipulators for Stability Using Topology Optimization," 2018 IEEE/RSJ International Conference on Intelligent Robots and Systems (IROS), Madrid, Spain, Oct. 1-5, 2018, pp. 1764-1769.

Souweidane et al., "Endoscopic resection of solid intraventricular brain tumors," Journal of Neurosurgery, Aug. 2006, vol. 105, pp. 271-278.

Souweidane et al., "Endoscopic Surgery for Intraventricular Brain Tumors in Patients Without Hydrocephalus," Operative Neurosurgery, Oct. 2005, vol. 57, No. 4, pp. ONS-312-ONS-318.

Teo et al., "Neuro-oncologic applications of endoscopy," Neurosurgery Clinics of North America, 2004, vol. 15, pp. 89-103.

* cited by examiner

Table 1. Optimized parameter values for three tubes comprising the robotic catheter. Tube sections are labeled in Fig. 4B.

|  | Tube 1 | Tube 2 | Tube 3 | |
|---|---|---|---|---|
|  | Section 1 | Section 1 | Section 1 | Section 2 |
| Outer diameter (mm) | 2.77 | 2.40 | 1.875 | 1.875 |
| Inner diameter (mm) | 2.54 | 2.00 | 1.60 | 1.60 |
| Section length (mm) | 72.0 | 72.0 | 55.0 | 72.0 |
| Radius of curvature (mm) | 150 | 150 | 40.0 | ∞ (straight) |
| Relative bending stiffness | 0.995 | 0.995 | 0.338 | 0.338 |

FIG. 5

AUTONOMOUS ROBOTIC CATHETER FOR MINIMALLY INVASIVE INTERVENTIONS

CROSS-REFERENCE TO RELATED APPLICATIONS

This application claims the benefit of and priority to U.S. Provisional Application No. 62/965,554, filed Jan. 24, 2020 which is hereby incorporated by reference in its entirety for all purposes.

FEDERALLY SPONSORED RESEARCH OR DEVELOPMENT

This invention was made with government support under Grant No. RO1 HL124020, awarded by the National Institutes of Health (NIH). The government has certain rights in the invention.

FIELD

The present disclosure relates to robotic systems designed to perform medical procedures and, in particular, autonomous robotic catheters for minimally invasive procedures within the body, such as brain and cardiac surgeries.

BACKGROUND

Minimally invasive surgery reduces the trauma associated with traditional open surgery, resulting in faster recovery time, fewer wound infections, reduced postoperative pain, and improved cosmesis. The trauma of open-heart surgery is particularly acute because it involves cutting and spreading the sternum to expose the heart. An important additional step to reducing procedural trauma and risk in cardiac procedures is to develop ways to perform repairs without stopping the heart and placing the patient on cardiopulmonary bypass.

To this end, many specialized devices have been designed that replicate the effects of open surgical procedures, but which can be delivered by catheter. These include transcatheter valves, mitral valve neochords, occlusion devices, stents, and stent grafts. To deploy these devices, catheters are inserted either into the vasculature (e.g., femoral vein or artery) or, via a small incision between the ribs, directly into the heart through its apex.

From the point of insertion, the catheter must be navigated to the site of the intervention inside the heart or its vessels. Beating-heart navigation is particularly challenging because blood is opaque and cardiac tissue is moving. Despite the difficulties of navigation, however, the most critical part of the procedure is device deployment. This is the component when the judgment and expertise of the clinician are most crucial. Much like the autopilot of a fighter jet, autonomous navigation can relieve the clinician from performing challenging, but routine, tasks so that they can focus on the mission-critical components of planning and performing device deployment.

To safely navigate a catheter, it is necessary to be able to determine its location inside the heart and to control the forces it applies to the tissue. In current clinical practice, forces are largely controlled by touch, whereas catheter localization is performed using fluoroscopy. Fluoroscopy provides a projective view of the catheter, but it does not show soft tissue and exposes the patient and clinician to radiation. Ultrasound, which enables visualization of soft tissue and catheters, is often used during device deployment, but the images are noisy and of limited resolution. In conjunction with heart motion, this makes it difficult to precisely position the catheter tip with respect to the tissue.

SUMMARY

The present disclosure relates to an autonomous robotic catheter for minimally invasive interventions. One such robotic system, in various embodiments, may comprise a robotic catheter steerable by a motorized drive system; an imaging device positioned on a distal end of the robotic catheter; and a controller configured to process one or more images captured by the imaging device to identify an anatomical feature, implanted device, or medical instrument in the one or more images, estimate a location of the imaging device in the body based on the identified anatomical feature, implanted device, or medical instrument, determine, based on the estimated location of the imaging device, a direction in which to steer the robotic catheter for advancement towards an interventional site, and monitor at least one of (i) a stream of images captured by the imaging device and (ii) force or distance measurements captured by the imaging device or by a sensor proximate the imaging device, to adjust the direction in which to steer the robotic catheter during advancement towards the interventional site.

The robotic catheter, in various embodiments, may be comprised of two or more concentric tubes. The motorized drive system, in various embodiments, may be operable to rotate and translate the robotic catheter.

The imaging device, in various embodiments, may include one of an image sensor, a camera, an ultrasonic probe, or other device configured to capture the one or more images. The controller, in various embodiments, may be configured to adjust the direction in which to steer the robotic catheter so as to maintain constant or intermittent contact with an anatomical feature during advancement towards the interventional site. In an embodiment, the imaging device may include a surface configured to displace bodily fluid from a contact interface between the imaging window and the anatomical feature, the implanted device, or the medical instrument. In another embodiment, the imaging device may include an imaging window covering the imaging device and the imaging window may include a surface configured to displace bodily fluid from a contact interface between the imaging window and the anatomical feature, implanted device, or medical instrument.

In various embodiments, processing one or more images captured by the imaging device may include comparing the one or more of the captured images to representative images of one or more anatomical features, implanted devices, or medical instruments present along a pathway to a interventional site.

In various embodiments, estimating a location of the imaging device in the body may include identifying the location of the identified anatomical feature, implanted device, or medical instrument in an anatomical model. In various embodiments, determining the direction in which to steer the robotic catheter for advancement towards a interventional site may include determining a vector between the estimated location of the imaging device and the interventional site using an anatomical model. The vector, in an embodiment, may be used in planning a path from the estimated location to the interventional site. The anatomical model, in some embodiments, may be non-dimensional. In an embodiment, the anatomical model may be obtained from pre-procedural or intraoperative imaging.

In various embodiments, monitoring a stream of images captured by the imaging device to adjust the direction in which to steer the robotic catheter may include identifying whether the imaging device is contacting the anatomical feature, implanted device, or medical instrument based on whether at least a portion of an image of the stream of images is unobstructed by bodily fluid. In various embodiments, monitoring a force measurement to adjust the direction in which to steer the robotic catheter may include determining whether the force measurement is substantially non-zero.

The controller, in various embodiments, may be configured to estimate a contact force between the imaging device and the anatomical feature based on how much of the one or more images is unobstructed by bodily fluid. In an embodiment, the controller may be configured to use the estimated contact force or the force measurement to avoid generating unsafe contact forces between the imaging device and the anatomical feature, the implanted device, or the medical instrument. In an embodiment, the controller may be configured to estimate an orientation of the imaging device relative to the anatomical feature based on a distribution of the contacting surface area with respect to a center of the image.

In various embodiments, monitoring a distance measurement to adjust the direction in which to steer the robotic catheter may include determining a distance to the anatomical feature, implanted device, or medical instrument. The controller may be configured to adjust the direction in which to steer the robotic catheter so as to avoid contact with an anatomical feature during advancement towards the interventional site.

In another aspect, the present disclosure is directed to a robotic system comprising a catheter; an imaging device positioned on the distal end of the catheter; and a processor configured to process one or more images captured by the imaging device to automatically perform at least one of the following: identify an anatomical feature, implanted device, or medical instrument contacted by the imaging device by comparing the one or more captured images to representative images of one or more anatomical features, implanted devices, or medical instruments present along a pathway to an interventional site, and estimate a contact force between the imaging device and the anatomical feature, implanted device, or medical instrument based on how much of the one or more images is unobstructed by bodily fluid.

In various embodiments, the catheter may be manually steered by a person. The processor, in various embodiments, may be configured to estimate a location of the imaging device in the body based on the identified anatomical feature, implanted device, or medical instrument. In various embodiments, estimating a location of the imaging device in the body based on the identified anatomical feature may include identifying the location of the identified anatomical feature, implanted device, or medical instrument in an anatomical model.

In various embodiments, the processor may be configured to determine, based on the estimated location of the imaging device, a direction in which to steer the catheter for advancement towards an interventional site. In an embodiment, determining the direction in which to steer the catheter for advancement towards a interventional site may include determining a vector between the estimated location of the imaging device and the interventional site using an anatomical model. The vector, in an embodiment, may be used in planning a path from the estimated location to the interventional site. The anatomical model, in various embodiments, may be non-dimensional. In an embodiment, the anatomical model may be obtained from pre-procedural or intraoperative imaging.

In various embodiments, the processor may be configured to use the estimated contact force to avoid generating unsafe contact forces between the imaging device and the anatomical feature, implanted device, or medical instrument. Additionally or alternatively, the processor, in an embodiment, may be configured to display, on a display device, one or more of the one or more captured images, the estimated location of the imaging device, the direction in which to steer the catheter for advancement towards the interventional site, and the estimated contact force.

BRIEF DESCRIPTION OF THE DRAWINGS

Illustrative, non-limiting example embodiments will be more clearly understood from the following detailed description taken in conjunction with the accompanying drawings.

FIG. 5 is a table showing the tube parameters of a representative robotic catheter;

DETAILED DESCRIPTION

Figure 1A:
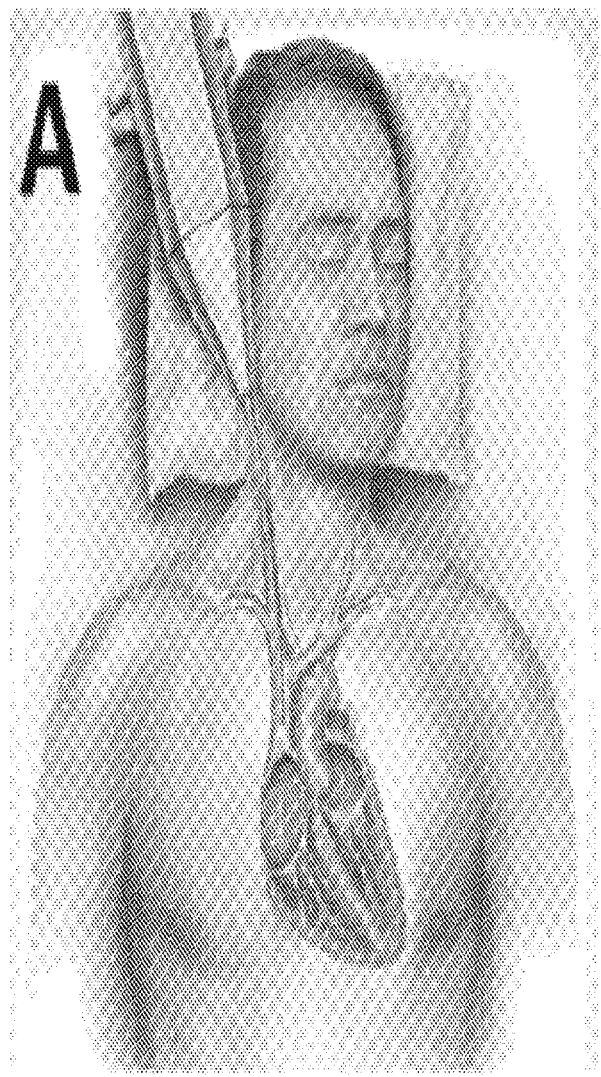
FIG. 1A and FIG. 1B illustrate a representative transjugular robotic catheter.

Embodiments of the present disclosure are directed to robotic systems for performing medical procedures and, in particular, minimally invasive procedures within the body such as brain and cardiac surgeries. The robotic systems described herein may be configured to autonomously navigate a robotic arm to an interventional site within the body. The use of autonomy can be applied in many catheter procedures. In the long term, autonomy may enable a senior clinician to safely oversee robots performing procedures on multiple patients simultaneously (concurrent surgery). In the shorter term, autonomous catheters will act as expert assistants to clinicians guiding them through both the routine and difficult parts of a procedure.

Embodiments of the present disclosure generally include a robotic arm or catheter and software that combines inputs from real-time and preoperative sensing together with a database including anatomical maps and machine learning algorithms that encode best practices for performing repairs. The robotic systems make procedures easier for clinicians by providing improved sensing (3D positioning and catheter shape visualization inside, e.g., the heart/vasculature) using multi-modal sensing including integrated optical, ultrasound, OCT, and force sensing, external sensing such as ultrasound, and intuitive catheter/device motion control. The robotic systems may be designed to send and receive data and algorithms from other robotic catheter devices and from other centralized data centers.

The robotic system incorporates procedural planning capabilities and, based on preoperative studies, such as imaging, proposes to the clinician an optimized set of repairs based on the available app's and hardware, e.g., to repair mitral regurgitation, it could propose annuloplasty together with a set of neochords (number, location on leaflets and attachment locations near or on papillary muscles). The clinician can accept these repairs and/or modify them such as by specifying alternate repairs and repair locations through the graphical interface. Once the clinician approves the overall plan, the robotic system would propose plans for each subtask on a graphical interface. These plans would be based on the robotic system's current autonomous motion algorithms. The clinician would have the option of approving or modifying the task motions. Once satisfied with a motion, the clinician can have the robot perform it autonomously or the operator can perform it via teleoperation. If by teleoperation, the robotic system can provide feedback, e.g., graphical and force feed long the desired path. This process would continue until all tasks are completed.

Various embodiments of the present disclosure may employ wall-following autonomous navigation techniques, as later described in more detail herein. In nature, wall following—tracing object boundaries in one's environment—is used by certain insects and vertebrates as an exploratory mechanism in low-visibility conditions to ameliorate their localization and navigational capabilities in the absence of visual stimuli. Positively thigmotactic animals, which attempt to preserve contact with their surroundings, use wall following in unknown environments as an incremental map-building function to construct a spatial representation of the environment. Animals initially localize new objects found by touch in an egocentric manner, i.e., the object's relative position to the animal is estimated; however, later, more complex spatial relations can be learned, functionally resembling a map representation. These animals often sample their environment by generating contact such as through rhythmically controlled whisker motion, as reported in rodents, or antennae manipulations in cockroaches and blind crayfish.

Such techniques may be applicable to many minimally invasive procedures including those in the vasculature, airways, gastrointestinal tract and the ventricular system of the brain. The catheter acts as a platform technology which can be adapted to new procedures or to the delivery of new devices by adding software/hardware applications. For example, a device for structural heart repair may offer software/hardware applications for mitral annuloplasty and for neochord placement. The device could also offer multiple software/hardware applications for the delivery of equivalent devices offered by different manufacturers, e.g., mitral clips. Besides structural heart repair, software/hardware applications can be provided for diagnostic angiograms, coronary stent delivery and aortic stent graft placement.

From a safety and learning standpoint, the robotic system's condition will be monitored in real-time by software that can identify and react to contingencies like hardware failures; either by shifting to teleoperation mode or by performing a pre-approved safety action (e.g., park at a safe location until the medical team provides new instructions).

The robotic system may collect data including (1) preoperative study data that was used for planning, (2) proposed and approved surgical plan, (3) input and output sensor data used by the robot, (4) operator commands, (5) robot planning and navigation algorithms used, and (6) procedure outcome data including, e.g., imaging studies. This data is used to refine both parametric and nonparametric models/algorithms of both the robotic system by itself and of the robot performing the specific procedure. Models and algorithms can be classified on the basis of a particular type of repair or more specifically, e.g., by a particular anatomical variation. The refined models and algorithms are then evaluated for safety following appropriate established protocols. Once approved, the models and algorithms on the robotic platform are updated for that procedure.

Model and algorithm refinement can be performed using only local data from a single robotic system. Alternately, it can pool data from a collection of robotic systems at, e.g., a single hospital, or from a large number of installed systems. In this way, the knowledge gained from every procedure performed is made available to all users and patients.

Figure 1B:
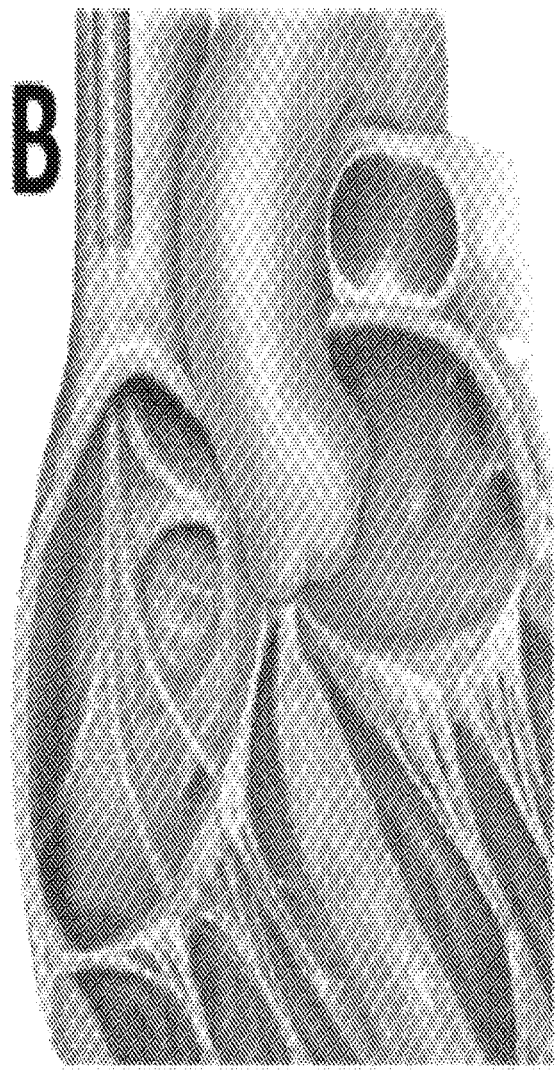

To show that autonomous navigation is possible, we investigated it in the hardest place to do it—inside the beating heart. FIG. 1A and FIG. 1B illustrate a representative transjugular robotic catheter of the present disclosure. In particular, FIG. 1A depicts the catheter passing through vasculature to the right atrium and FIG. 1B illustrates how the design of telescoping robotic catheter modules allows the robotic catheter to be steered to and about the interventional site.

We created a robotic catheter that can navigate through the blood-filled heart using wall-following algorithms inspired by positively thigmotactic animals. The catheter uses haptic vision, a hybrid sense using imaging for both touch-based surface identification and force sensing, to accomplish wall following inside the blood-filled heart. Through in vivo animal experiments, we demonstrate that the performance of an autonomously controlled robotic catheter rivaled that of an experienced clinician. Autonomous navigation is a fundamental capability on which more sophisticated levels of autonomy can be built, e.g., to perform a procedure. Similar to the role of automation in a fighter aircraft, such capabilities can free the clinician to focus on the most critical aspects of the procedure while providing precise and repeatable tool motions independent of operator experience and fatigue.

Inspired by this approach, we designed positively thigmotactic algorithms that achieve autonomous navigation inside the heart by creating low-force contact with the heart tissue and then following tissue walls to reach a goal location. To enable wall following while also locally recapturing the detailed visual features of open surgery, we introduced a sensing modality at the catheter tip that we call "haptic vision." Haptic vision combines intracardiac endoscopy, machine learning, and image processing algorithms to form a hybrid imaging and touch sensor—providing clear images of whatever the catheter tip is touching while also identifying what it is touching (e.g., blood, tissue, and valve) and how hard it is pressing.

Our primary result is that autonomous navigation in minimally invasive procedures is possible and can be successfully implemented using enhanced sensing and control techniques to provide results comparable with expert manual navigation in terms of procedure time and efficacy. Furthermore, our experiments comparing clinician-controlled robotic navigation with manual navigation echo the results obtained for many medical procedures—robots operated by humans often provide no better performance than manual procedures except for the most difficult cases and demanding procedures. Medical robot autonomy provides an alternative approach and represents the way forward for the field.

Automating such tasks as navigation can provide important benefits to clinicians. For example, when a clinician is first learning a procedure, a significant fraction of their attention is allocated to controlling instruments (e.g., catheters and tools) based on multimodal imaging. Once a clinician has performed a large number of similar procedures with the same instruments, the amount of attention devoted to instrument control is reduced. By using autonomy to relieve the clinician of instrument control and navigation, the learning curve involved in mastering a new procedure could be substantially reduced. This would be of significant benefit during initial clinical training, and it may also enable midcareer clinicians to adopt new minimally invasive techniques that would otherwise require too much retraining. In addition, even after a procedure is mastered, there are many situations where an individual clinician may not perform a sufficient number of procedures to maintain mastery of it. In all of these cases, autonomy could enable clinicians to operate as experts with reduced experience- and fatigue-based variability.

There are also many places in the world where clinical specialties are not represented. Although medical robots can provide the capability for a specialist to perform surgery remotely, this approach requires dedicated high-bandwidth two-way data transfer. Transmission delays or interruptions compromise safety owing to loss of robot control. In these situations, autonomy may enable stable and safe robot operation even under conditions of low-bandwidth or intermittent communication. Autonomy may also enable the robot to detect and correct for changing patient conditions when communication delays preclude sufficiently fast reaction by the clinician.

Autonomy also enables, to an unprecedented degree, the capability to share, pool, and learn from clinical data. With teleoperated robots, robot motion data can be easily collected, but motions are being performed by clinicians using different strategies, and the information they are using to guide these strategies may not all be known, let alone recorded. In contrast, the sensor data streaming to an autonomous controller are well defined, as is its control strategy. This combination of well-defined input and output data, together with known control strategies, will make it possible to standardize and improve autonomous technique based on large numbers of procedural outcomes. In this way, robot autonomy can evolve by applying the cumulative experiential knowledge of its robotic peers to each procedure.

Robotic System 100

Figure 2:
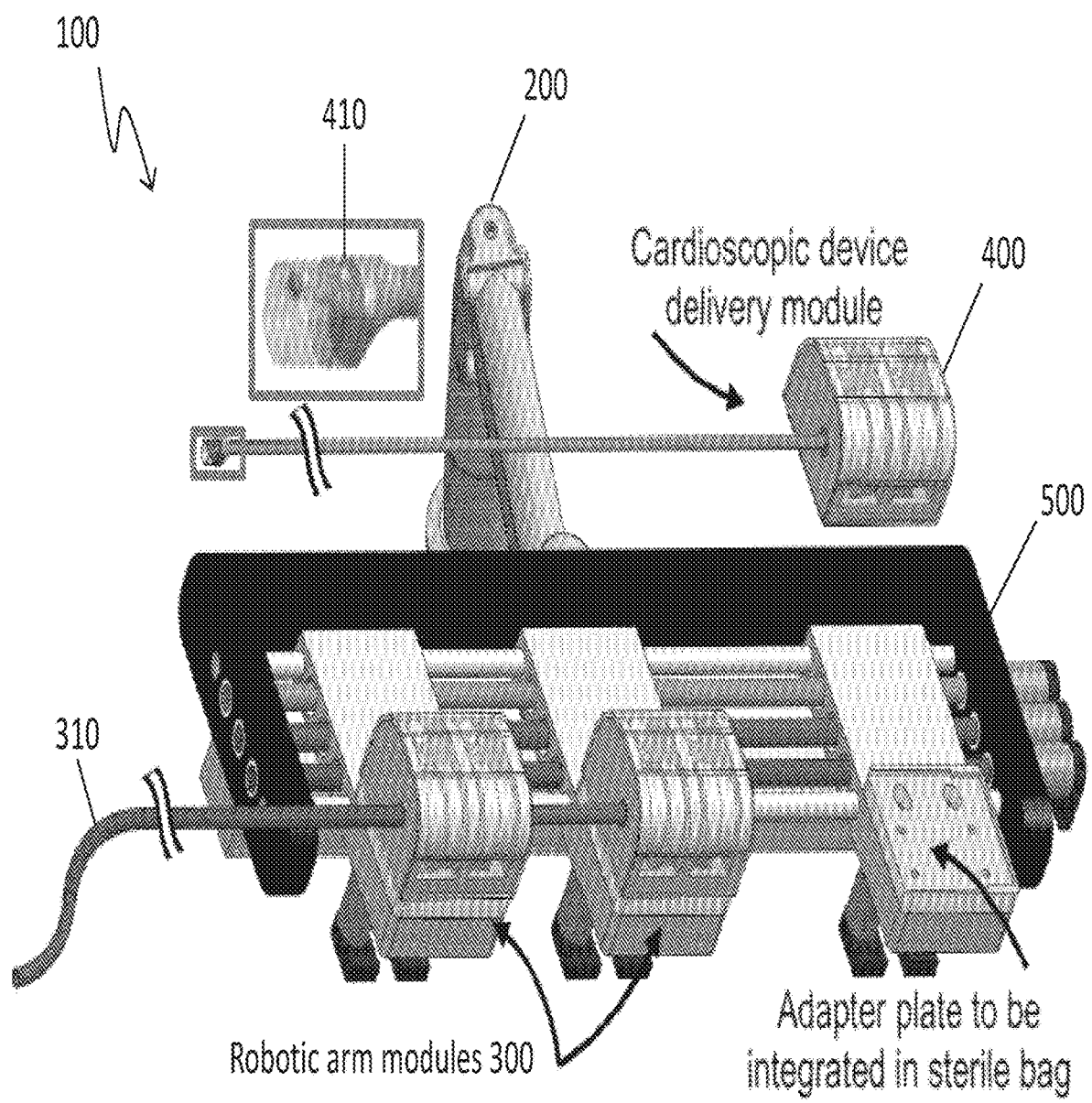
FIG. 2 depicts a representative embodiment of a robotic system including a support structure, one or more robotic arm modules, one or more tool modules, and a drive system.

FIG. 2 depicts a representative embodiment of robotic system 100. Robotic system 100 of the present disclosure may generally include a support structure 200, one or more robotic arm modules 300, one or more tool modules 400, and a drive system 500. In various embodiments, each robotic arm module 300 and tool module 400 may detachably couple to support structure 200 and are operated by drive system 500 to perform a surgical procedure. Robotic arm module(s) 300 may include a robotic arm 310 having working channel 311 (not shown) for accommodating an elongate tool 410 of tool module 400 and robotic arm 310 can be steered about a interventional site to position and orient a distal end of elongate tool 410 during the procedure. As configured, elongate tool 410, in various embodiments, may be removed from working channel 311 of robotic arm 310 during the procedure without having to withdraw robotic arm module 300 from the interventional site, thereby allowing tool modules 400 to be swapped in and out during a procedure and medical devices (e.g., stents) to be implanted through working channel 311 with ease and speed. Components of robotic system 100, in various embodiments, may be analogous to those of the robotic device described in U.S. Provisional Patent Application No. 62/965,399 filed Jan. 24, 2020, which is incorporated by reference herein in its entirety.

Figure 3:
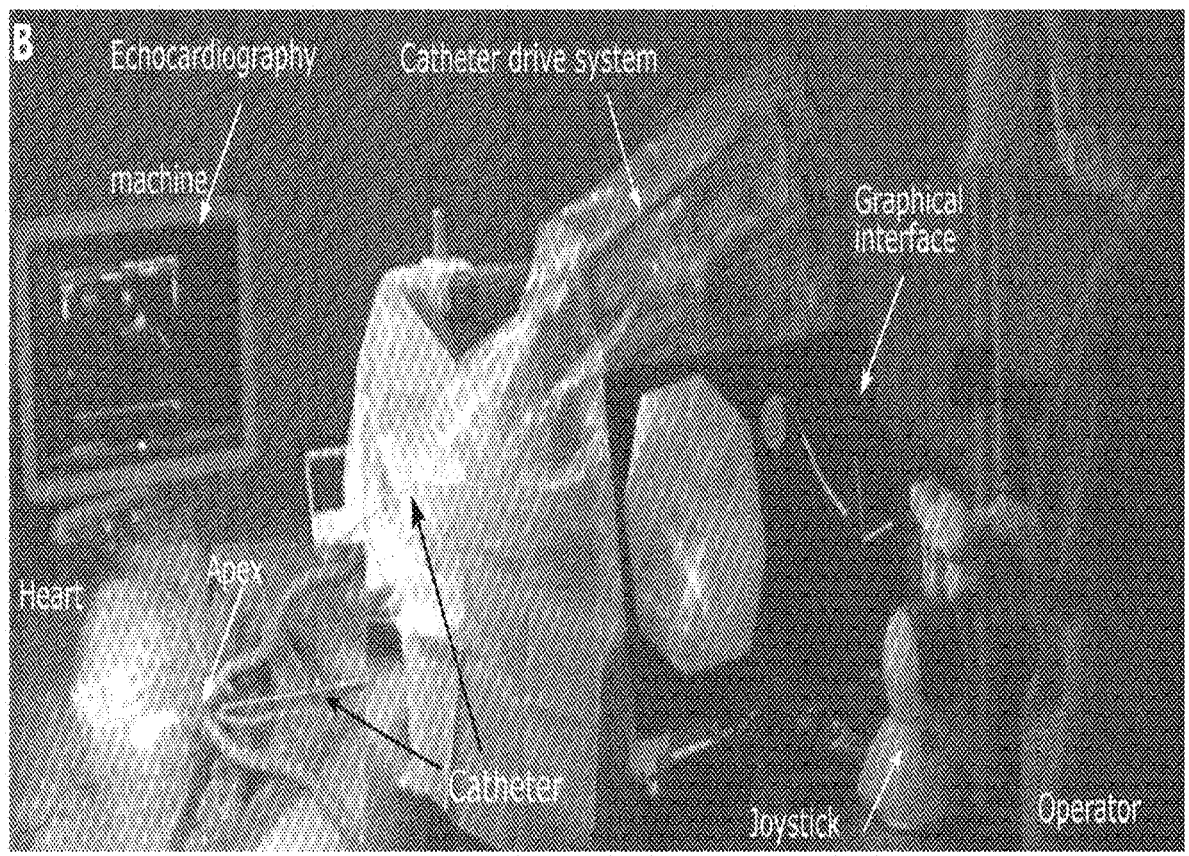
FIG. 3 shows a drive system mounted on the operating room table using a passively adjustable frame that allows the catheter tip to be positioned and oriented for entry into the apex.

For the specific autonomous navigation experiments described below, we designed the catheter using concentric tube robot technology in which robots are composed of multiple needle-sized concentrically combined precurved superelastic tubes. A motorized drive system located at the base of the tubes rotated and telescopically extended the tubes with respect to each other to control the shape of the catheter and its tip position. The drive system was mounted on the operating room table using a passively adjustable frame that allowed the catheter tip to be positioned and oriented for entry into the apex (FIG. 3).

Figure 4:
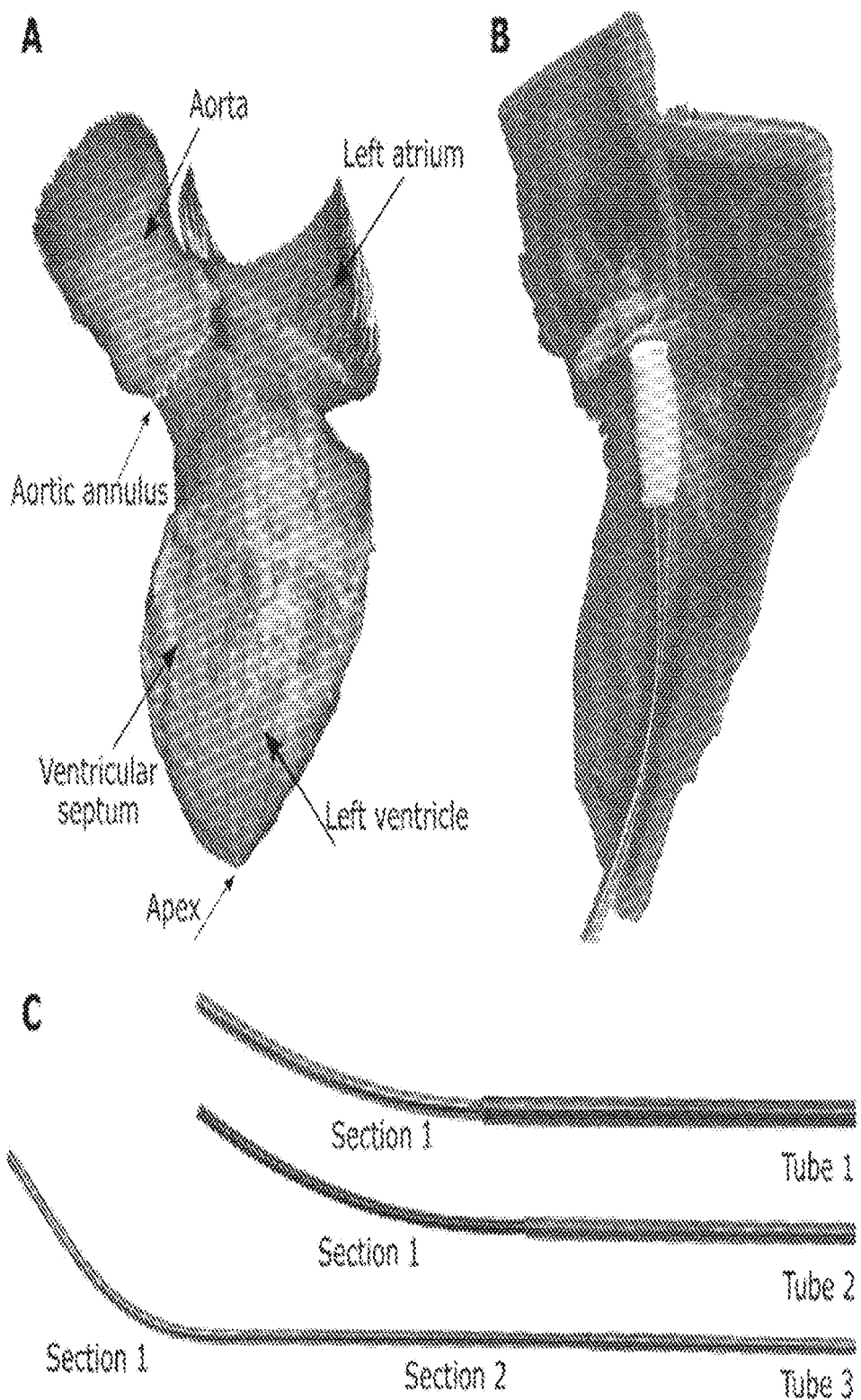
FIG. 4 illustrates a 3D model of an adult human left ventricle.

Tools and devices were delivered through the lumen of the innermost robot tube, which incorporated a valve and flush system at its proximal end. This system enabled the catheter lumen to be flushed with saline to prevent air entry into the heart and to prevent pressurized blood from the heart from entering the lumen of the catheter. We used a design optimization algorithm to solve for the tube parameters based on the anatomical constraints and clinical task (e.g., aortic paravalvular leak closure). The anatomical and task constraints were defined using a 3D model of an adult human left ventricle (FIG. 4). Because the relative dimensions of the human and porcine hearts are similar, the resulting design was appropriate for our in vivo experiments. The design algorithm solved for the tube parameters enabling the catheter tip to reach from the apex of the heart to a set of 25 uniformly sampled points around the aortic valve annulus without the catheter contacting the ventricular wall along its length. The orientation of the catheter tip was further constrained at the 25 points to be within 100 of orthogonal to the valve plane. The resulting design was composed of three precurved superelastic tubes forming two telescoping sections with motion as shown in FIG. 4. The tube parameters of the robotic catheter are given in FIG. 5.

Haptic Vision Sensor 410

Figure 6:
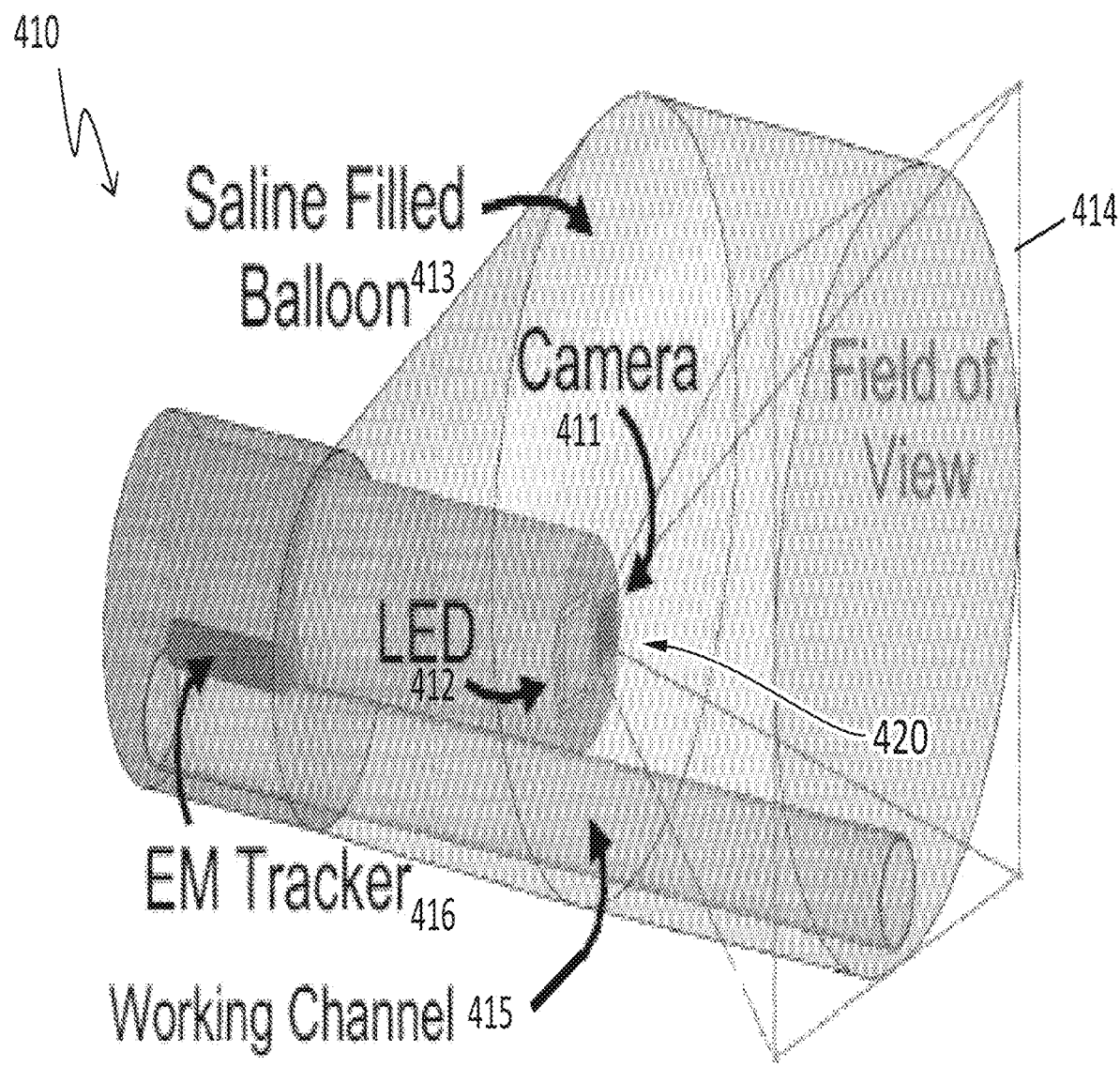
FIG. 6 depicts a representative embodiment of the haptic vision sensor.

FIG. 6 depicts a representative embodiment of haptic vision sensor 410 of the present disclosure. Haptic vision sensor 410, in various embodiments, may generally comprise an imaging device 411 such as an image sensor (e.g., charge-coupled device (CDD) or complementary metal oxide semiconductor (CMOS)), a camera, an ultrasonic probe, or other device configured to capture one or more images. Sensor 410, in various embodiments, may optionally include a light source 412 and/or an imaging window 413 covering imaging device 411. Imaging window 413, in various embodiments, may be transparent and positioned in front of imaging device 411 to seal off a space in front of imaging device 411 from surrounding bodily fluids for improved visibility, much like a snorkeling mask. Together, these components combine to define a field of view 414 of imaging device 411.

As later described in more detail, robotic system 100 may employ wall-following techniques to autonomously navigate to a interventional site in the body. Haptic vision sensor 410, in various embodiments, may continuously or intermittently contact tissue and other anatomical features within the body to assess where it is and which direction to go next. When haptic vision sensor 410 is pressed against the tissue, it displaces blood or other bodily fluids obstructing the field of view 414 of imaging device 411. Generally speaking, higher contact force displaces more fluid from the contact interface between imaging window 413 and the tissue or displaces fluid over a greater portion of the cardiac cycle, thereby increasing the amount of tissue visible to imaging device 411, and vice versa. Accordingly, in various embodiments, the amount of tissue visible in the field of view 414 of imaging device 411 may serve as a proxy for estimating contact force.

In various embodiments, robotic system 100 may be configured to analyze images captured by imaging device 411 to determine a location of haptic vision sensor 410 within the body. As later described in more detail, robotic system 100 may use any number of suitable image processing techniques to compare a captured image with images stored in a database of various tissues and anatomical features to identify a likely match and thereby determine a location of haptic vision sensor 410 within the body. Accordingly, haptic vision sensor 410 may act as a combined sensor for detecting contact, estimating contact force, and determining a location of haptic vision sensor 410 within the body based on images captured by imaging device 411.

Still referring to FIG. 6, robotic system 100, in various embodiments, may further comprise a working channel 415 through which a tool or other device may be advanced to the interventional site. As configured, tool module 400 need not necessarily be removed from robotic arm 310 in order to make room for advancing the tool or other device to the interventional site through working channel 311 of robotic arm 310. Instead, haptic vision sensor 410 may remain in place when using the tool and advantageously allow an operator (e.g., surgeon) to see the tool and/or interventional site via imaging device 411 during the procedure. Additionally or alternatively, robotic system 100, in various embodiments, may further comprise an electromagnetic tracker 416. As later described in more detail, the kinematic model of the catheter may be used to determine the location of the catheter tip in space. Since the catheter deforms owing to contact with the anatomy, however, this estimate can be inaccurate. A tip-mounted tracking sensor or a catheter shape sensor that computes the actual shape of the catheter can be used to provide more accurate measurements of tip location. These measurements can be used to build an anatomical map as described later in the application (valve annulus model). They can also be used together with imaging-based anatomic feature identification to localize the catheter tip with respect to an anatomic model, perform registration of the anatomic model with respect to the robot and the patient, to scale the anatomic model with respect to the patient and to guide motion toward the procedural target.

Figure 7:
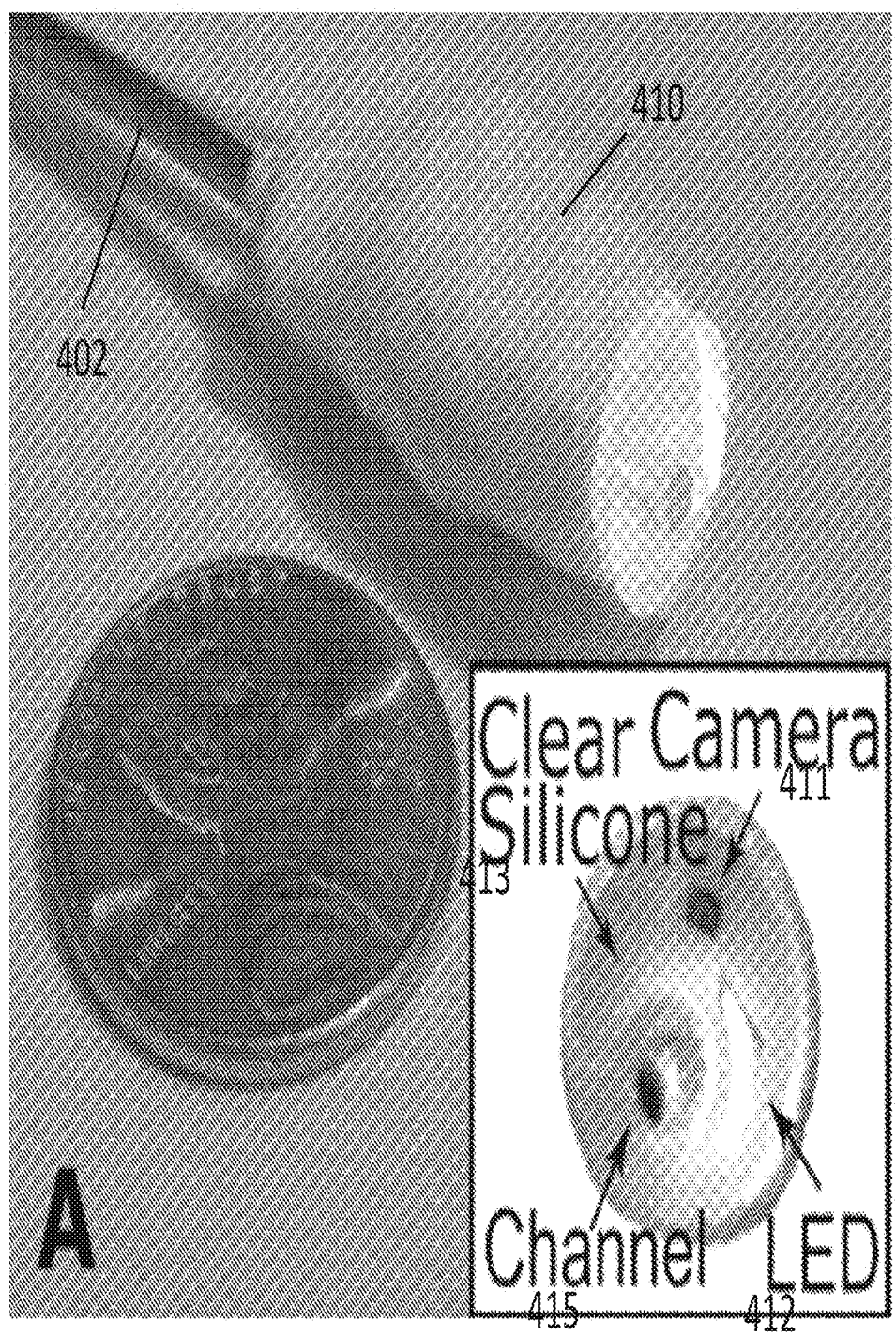
FIG. 7 illustrates a representative embodiment of the haptic vision sensor next to a penny for scale.

FIG. 7 shows a representative embodiment of haptic vision sensor 410 next to a penny for scale. We fabricated this prototype of sensor 410 using a 1-mm$^3$ complementary metal-oxide semiconductor imaging device 411 (NanEye Camera System, AWAIBA) and a 1.6 mm by 1.6 mm light-emitting diode 412 (XQ-B LED, Cree Inc.) encased in an 8-mm-diameter silicone imaging window 414 (QSil 218, Quantum Silicones LLC.) molded onto a stainless-steel body. The diameter of imaging window 414 was selected to provide a field of view 414 facilitating both autonomous and operator-guided navigation. Sensor 410 also incorporated a 2.5-mm-diameter working channel 415 for device delivery. Sensor 410 is clamped to the tip of the catheter 402 such that the lumen of the innermost catheter tube is aligned with working channel 415. Although we have also designed catheters 402 in which the sensor wiring was run through the catheter lumen, in these experiments, the wiring for the imaging device 411 and LED 412 were run outside so that sensor 410 could be replaced without disassembling robotic system 100. Note that FIG. 2 shows an alternate design in which the cardioscope is designed to pass through the robotic catheter.

Wall-Following Autonomous Navigation

As previously noted, robotic system 100 may employ wall-following techniques to autonomously navigate to a interventional site in the body. Robotic system 100, in various embodiments, may include a controller configured to steer the robotic catheter in a manner that causes it to continuously or intermittently contact anatomical features within the body to assess where it is and which direction to go next in order to reach the interventional site. In various embodiments, controller may utilize information captured or collected by haptic vision sensor 410 to this and related ends, as described in more detail below.

The controller, in various embodiments, may be configured to process one or more images captured by imaging device 411 to identify an anatomical feature contacted by imaging device 411. As used herein, the term "anatomical feature" broadly refers to solid anatomical features like tissues, organs, and the like (as opposed to bodily fluids) that may be present along a pathway (e.g., one defined by the vasculature) to the interventional site. As described in more detail below, the controller may be configured to compare the one or more of the images captured by imaging device 411 to representative images of anatomical features present along a pathway to a interventional site. The representative images may be stored in a database accessed by the controller and the controller may parse through the images until it identifies a likely match with the captured image. Machine learning techniques may be used in this process as later described in more detail. Upon identifying a match, the controller may determine where the identified anatomical feature is in a representative anatomical model and thus understand where imaging device 411 is in the body. The controller may use similar techniques to identify when it has reached a medical device/instrument or implant (e.g., a prosthetic valve) in the body. In various embodiments, the controller may be configured to steer the system such that it follows a surface(s) of the medical device/instrument or implant similar to the way in which it may follow an anatomical feature/tissue to the interventional site.

The controller, in various embodiments, may also use the estimated location of imaging device 411 along with the anatomical model to determine a direction in which to steer the robotic catheter for advancement towards a particular interventional site. In particular, the controller may be configured to identify a suitable pathway in the anatomical model (e.g., a particular artery or vein, or pathway through the chambers of the heart) that extends between the estimated location of imaging sensor 411 and the interventional site, and thereby determine a direction in which to direct the robotic catheter to follow that pathway generally. In an embodiment, the anatomical model is non-dimensional, thereby allowing it to be used with persons of varying shapes and sizes.

The controller, in various embodiments, may use tip tracking sensors or catheter shape sensors to track its motion and use the data to validate and refine its estimated position and orientation with respect to an anatomical model. It may also use this data to adjust the size and shape of a dimensionless anatomical model to fit that of a patient. It can also use this data to create an anatomical map as described later in the application. Furthermore, it can use the motion data to guide its advancement toward a procedural site.

The controller, in an embodiment, may be further configured to estimate an orientation of imaging device 411 relative to an anatomical feature and use this as an additional input to facilitate steering the robotic catheter. In particular, if the feature is locally planar, the surface normal to the plane may be estimated from the images. If, furthermore, the sensor is in contact with the feature, the distribution of the contacting surface area with respect to the center of the image can be used to estimate the relative orientation.

The controller, in various embodiments, may adjust the direction in which the robotic catheter is being steered in order to maintain intermittent or continuous contact with surrounding anatomical features during advancement towards the interventional site as part of a wall-following navigation approach. In particular, in various embodiments, controller may monitor at least one of (i) a stream of images captured by imaging device 411, and (ii) a force measurement captured by a sensor proximate the imaging device, to determine whether image sensor 411 is in contact with an anatomical feature. With respect to (i), as previously described, when image sensor 411 contacts an anatomical feature, bodily fluid is displaced from the contact interface such that all or a portion of the image contains an unobstructed view of the anatomical feature. Accordingly, if all or a portion of a given image is unobstructed by bodily fluid, the controller may determine that imaging device 411 is in contact with an anatomical feature. Conversely, if the entire image is obstructed by bodily fluid, the controller may determine that imaging device 411 is not in contact with an anatomical feature. Regarding (ii), the controller may determine that image sensor 411 is in contact with an anatomical feature if the force measurement is substantially non-zero and not in contact with an anatomical feature if the force measurement is substantially zero.

The controller, in various embodiments, may use information about whether imaging sensor 411 is in contact with the anatomical feature to adjust the direction in which to steer the robotic catheter in accordance with a particular wall-following technique being utilized. For example, in embodiments employing continuous contact wall following techniques, the controller may adjust the direction of the robotic catheter back towards the anatomical feature (or towards an upcoming anatomical feature, as predicted from the anatomical map or otherwise) if the controller detects that imaging device 411 is no longer in contact with the anatomical feature. As another example, in embodiments employing intermittent contact wall following techniques, the controller may adjust the direction of the robotic catheter back towards the anatomical feature after a predetermined period of time or distance travelled to again establish contact with the anatomical feature, where it can again estimate the location of imaging sensor 411 and thereby confirm whether adjustments to the general steering direction need to be made to successfully navigate to the interventional site.

The controller, in various embodiments, may additionally or alternatively estimate the associated contact force. When imaging device 411 is pressed against the tissue, it displaces blood or other bodily fluids obstructing the field of view 414 of imaging device 411. Generally speaking, higher contact forces displace more fluid from the contact interface, thereby increasing the portion of the image in which the anatomical feature is visible and unobstructed by bodily fluid, and vice versa. Accordingly, in various embodiments, the size of an unobstructed portion of an image may serve as a proxy for estimating contact force. In another embodiment, the aforementioned force sensor may additionally or alternatively provide force measurements indicating the contact force. The controller may use the estimated contact force or the force measurement to avoid generating unsafe contact forces between imaging device 411 and an anatomical feature. For example, the controller may cease advancing the robotic catheter in a current direction if the estimated or measured contact force exceeds a predetermined threshold for safety. It should be recognized that such thresholds may vary based on the particular anatomical feature identified as being contacted.

It should be recognized that while the present disclosure describes autonomous robotic navigation techniques, robotic system 100 may be adapted to facilitate manual steering of a catheter. Such a manual system may comprise a traditional catheter or a manually-steered robotic catheter (e.g., manually steerable by joystick, as opposed to autonomously steered by the controller), an imaging device 411 positioned on the distal end of catheter 402, and a processor. Generally speaking, the processor may perform analytical functions similar to those of the controller, but rather than automatically steering the catheter, the processor may display or otherwise provide information to a person steering the catheter to facilitate manual steering. For example, the processor may be configured to display on a display device in the operating room one or more of the navigation-related parameters described above—that is, the estimated location and orientation of imaging device 411, a suggested direction in which to steer the catheter, suggested adjustments to the direction to reestablish or maintain contact with surrounding anatomy depending on whether intermittent or continuous wall-following techniques are to be employed, etc. derived as explained above. Such a system could also provide warnings to the operator if contact forces (estimated or measured) may exceed safety thresholds.

Navigation Experiment

Figure 8:
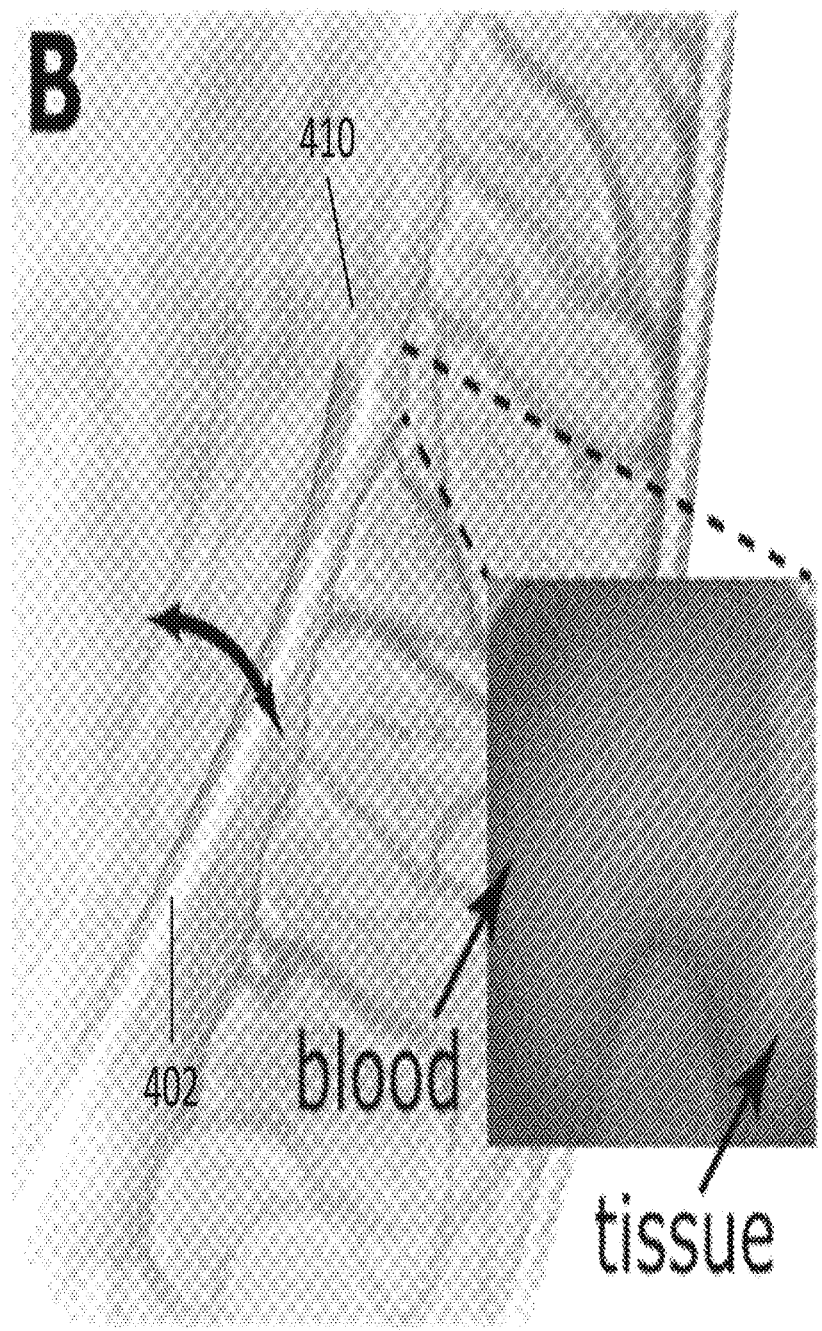
FIG. 8 shows the robotic catheter tip pressed laterally against cardiac tissue.
Figure 9:
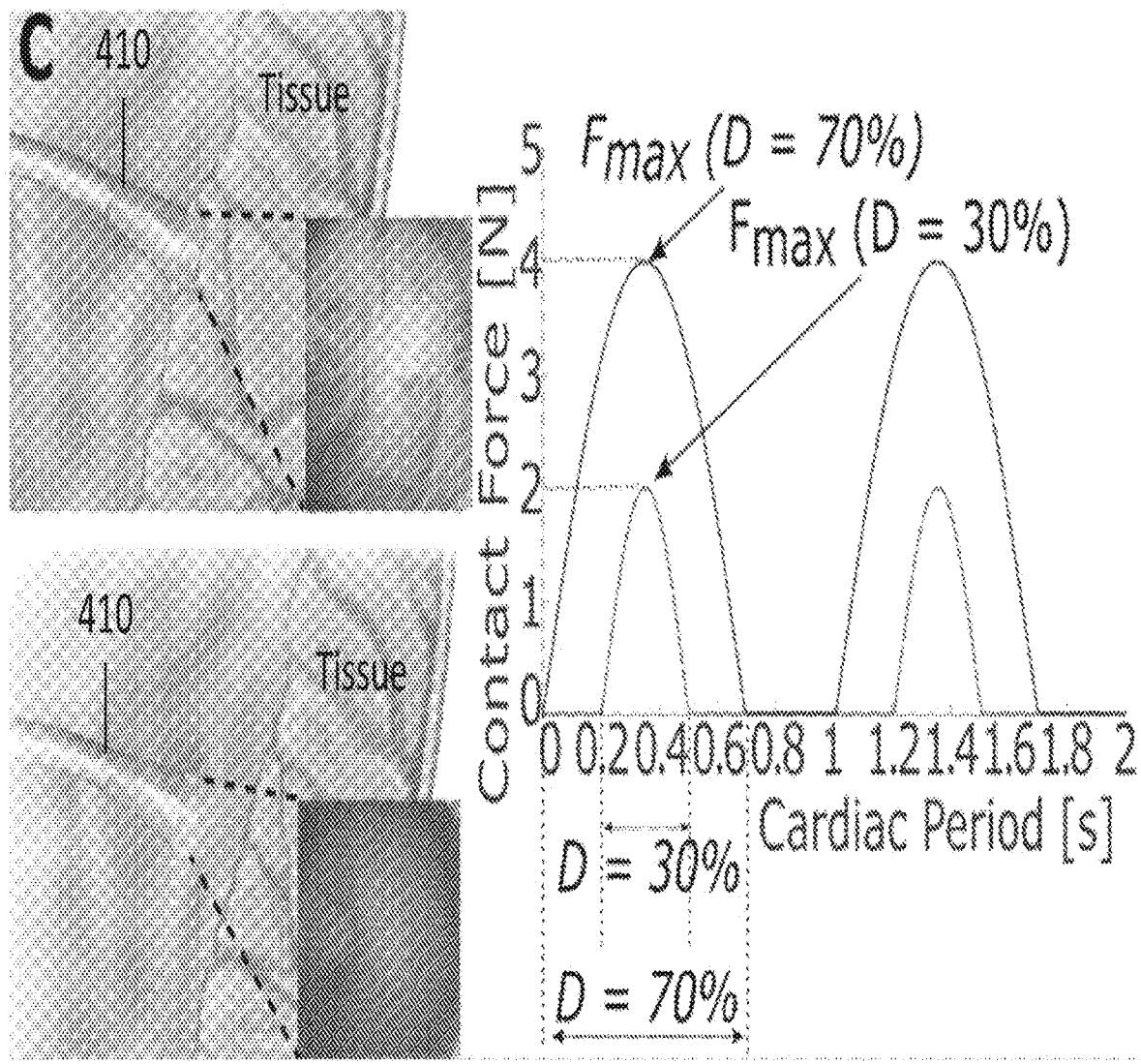
FIG. 9 depicts the robotic catheter being operated in an intermittent contact mode in which the catheter is in contact with the heart wall for a specified fraction of the cardiac period.

In an experiment, we used haptic vision as the sole sensory input to our navigation algorithms to achieve wall following while also controlling the forces applied by the catheter tip to the tissue. We evaluated autonomous navigation through in vivo experiments and compared it with operator-controlled robot motion and with manual navigation. For wall following, we exploited the inherent compliance of the catheter to implement two control modes based on continuous and intermittent contact. Continuous contact can often be safely maintained over the cardiac cycle when the catheter tip is pressed laterally against the tissue because catheters are highly compliant in this direction (FIG. 8). Intermittent contact can be necessary when there is substantial tissue motion and the catheter is against the tissue along its stiffer longitudinal axis (FIG. 9).

To perform wall following, we designed a machine learning-based image classifier that can distinguish between blood (no contact), ventricular wall tissue, and the bioprosthetic aortic valve. The algorithm used the bag-of-words approach to separate images into groups (classes) based on the number of occurrences of specific features of interest. During training, the algorithm determined which features were of interest and the relationship between their number and the image class. For training, we used OpenCV to detect features in a set of manually labeled training images. Next, the detected features were encoded mathematically using LUCID descriptors for efficient online computation. To reduce the number of features, we identified the optimal feature representatives using clustering (k-means). The resulting cluster centers were the representative features used for the rest of the training, as well as for runtime image classification. Having identified the set of representative features, we made a second pass through the training data to build a feature histogram for each image by counting how many times each representative feature appeared in the image. The final step was to train a support vector machine (SVM) classifier that learned the relationship between the feature histogram and the corresponding class.

Using the trained algorithm, image classification proceeded by first detecting features and computing the corresponding LUCID descriptors. The features were then matched to the closest representative features, and the resulting feature histogram was constructed. On the basis of the histogram, the SVM classifier predicted the tissue-based contact state. We achieved good results using a small set of training images (~2000 images) with training taking ~4 min. Because image classification took 1 ms, our haptic vision system estimated contact state at the frame rate of the camera (45 frames/s). The contact classification algorithm was accurate 97% of the time (tested on 7000 images not used for training) with type I error (false positive) of 3.7% and type II (false negative) of 2.3%.

In both the continuous and the intermittent contact modes, the robot acted to limit the maximum force applied to the tissue using a haptic vision-based proxy for force. In the continuous contact mode, catheter position with respect to the tissue surface was adjusted to maintain a specified contact area on the catheter tip (FIG. 8) corresponding to a desired force. In the intermittent contact mode, catheter position with respect to the tissue surface was adjusted to maintain a desired contact duty cycle—the fraction of the cardiac cycle during which the catheter was in tissue contact (FIG. 9). The relationship between contact duty cycle and maximum force was investigated experimentally as described in the section below titled "In-vivo calibration of contact duty cycle versus maximum tissue force." Complex navigation tasks can be achieved by following a path through a connectivity graph (FIG. 10) and selecting between continuous and intermittent contact modes along that path based on contact compliance and the amplitude of tissue motion.

FIG. 8 depicts the robotic catheter 100 being operated in a continuous contact mode in which catheter tip is pressed laterally against heart wall over entire cardiac motion cycle. Contact force is controlled on the basis of the amount of tissue visible at the edge of imaging window as shown in inset.

When the catheter was positioned laterally against cardiac tissue, its flexibility could enable continuous contact to be maintained without applying excessive force to the tissue. We used haptic vision to control the amount of tissue contact by controlling catheter motion in the direction orthogonal to the tissue surface. Catheter motion in the plane of the tissue surface was independently controlled so as to produce wall following at the desired velocity and in the desired direction. The controller was initialized with an estimate of wall location so that if it was not initially in tissue contact, it moved toward the wall to generate contact. This occurred in our in vivo experiments during navigation from the apex to the aortic valve. The catheter started in the center of the apex with the haptic vision sensor detecting only blood. It would then move in the direction of the desired wall (FIG. 10, a→b), specified using valve clock coordinates (FIG. 12), to establish contact and then follow that wall until it reached the valve.

When the haptic vision sensor 410 was pressed laterally against the tissue, the tissue deformed around the sensor tip so that it covered a portion of the field of view 414 (FIG. 8). The navigation algorithm adjusted the catheter position orthogonal to the tissue surface to maintain the centroid of the tissue contact area within a desired range on the periphery of the image, typically 30 to 40%. We implemented tissue segmentation by first applying a Gaussian filter to reduce the level of noise in the image. Next, we segmented the tissue using color thresholding on the hue saturation value (HSV) and the CIE L*a*b* representations of color images. The result was a binary image, where white pixels indicated tissue. Last, we performed a morphological opening operation to remove noise from the binary image. After segmentation, the tissue centroid was computed and sent to the motion control computer. Image processing speed was sufficient to provide updates at the camera frame rate (45 frames/s).

FIG. 9 depicts the robotic catheter 100 being operated in an intermittent contact mode in which catheter is in contact with heart wall for a specified fraction, D, of the cardiac period (contact duty cycle). Insets show corresponding haptic vision images in and out of contact. Maximum contact force relates to contact duty cycle, D, as shown on plot and is controlled by small catheter displacements orthogonal to the heart wall.

When a catheter is stiff along its longitudinal axis and positioned orthogonal to a tissue surface that moved significantly in the direction of this axis over the cardiac cycle, the contact forces can become sufficiently high so as to result in tissue damage or puncture. To maintain contact forces at safe levels, one approach is to design the catheter so that it can perform high-velocity trajectories that move the robotic catheter tip in synchrony with the tissue. We used an alternative technique requiring only slow catheter motion so as to position the tip such that it was in contact with the tissue for a specified fraction of the cardiac cycle, the contact duty cycle, D (FIG. 9). As described in the section below titled "In-vivo calibration of contact duty cycle versus maximum tissue force," the contact duty cycle was linearly related to the maximum contact force. The intermittent contact mode was used during navigation around the aortic valve annulus.

We implemented intermittent contact navigation using haptic vision to detect tissue contact and, combined with heart rate data, to compute the contact duty cycle at the frame rate of the camera (45 frames/s). We implemented a controller that adjusted catheter position along its longitudinal axis to drive the contact duty cycle to the desired value. Catheter motion in the plane of the tissue surface was performed either autonomously or by the operator (shared control mode). In the autonomous mode, catheter motion in the tissue plane was performed only during the fraction of the cardiac cycle when the haptic vision sensor indicated that the catheter was not touching tissue. This reduced the occurrence of the catheter tip sticking to the tissue surface during wall following.

Example 1—Autonomous Navigation on Prosthetic Aortic Heart Valve Annulus

Intermittent contact control was used to control catheter motion orthogonal to the plane of the annulus. The desired value of contact duty cycle was typically set to be ~40%. Thus, 40% of the cardiac cycle was available for image processing (during contact), whereas the motion in the plane of the annulus was performed during the 60% noncontact portion of the cardiac cycle. During contact, the robot detected the blue tangent sutures on the valve (FIG. 12) using color thresholding in the HSV color space and computed the centroid of the detected sutures. Next, a Hough transform on the thresholded image was used to estimate the tangent of the aortic annulus. During the noncontact portion of the cardiac cycle, the algorithm generated independent motion commands in the radial and tangential directions. In the radial direction, the catheter adjusted its position such that the centroid of the detected sutures was centered in the imaging frame. Motion in the tangential direction was performed at a specified velocity. While navigating around the valve, the robot incrementally built a map of the location of the annulus in 3D space based on the centroids of the detected sutures and the catheter tip coordinates as computed using the robot kinematic model. The model was initialized with the known valve diameter and the specified direction of approach. By comparing the current tangent with the model/map, the robot estimated its clock position on the annulus. Although not implemented, this model may also be used to estimate the valve tangent and radial position in situations where the sutures are not well detected.

To autonomously move to a prespecified location on the valve, it is necessary to know how the valve is rotated with respect to the catheter tip. In the ventricular view of the valve annulus provided by haptic vision, such features are hidden. Although the model built during annular navigation defines the coordinates of the annulus circle in 3D space, there was no means to refine the initial estimate of where 12 o'clock fell on the circle, i.e., to establish the orientation of the valve about its axis. To enable the robot to refine its orientation estimate, we introduced registration features into the annulus composed of green sutures located at 4, 8, and 12 o'clock. During annular navigation, whenever the robot detected one of these features, it compared its actual location with the current prediction of the model and updated its estimate of valve rotation accordingly.

In clinical use, the sutures would remain visible for several months before endothelialization. Thus, they could be used for autonomous repair of paravalvular leaks (as described below) that occur at the time of valve implantation or soon after, as is the case for transcatheter valves.

Example 2—Autonomous Navigation for Paravalvular Leak Closure

Figure 11:
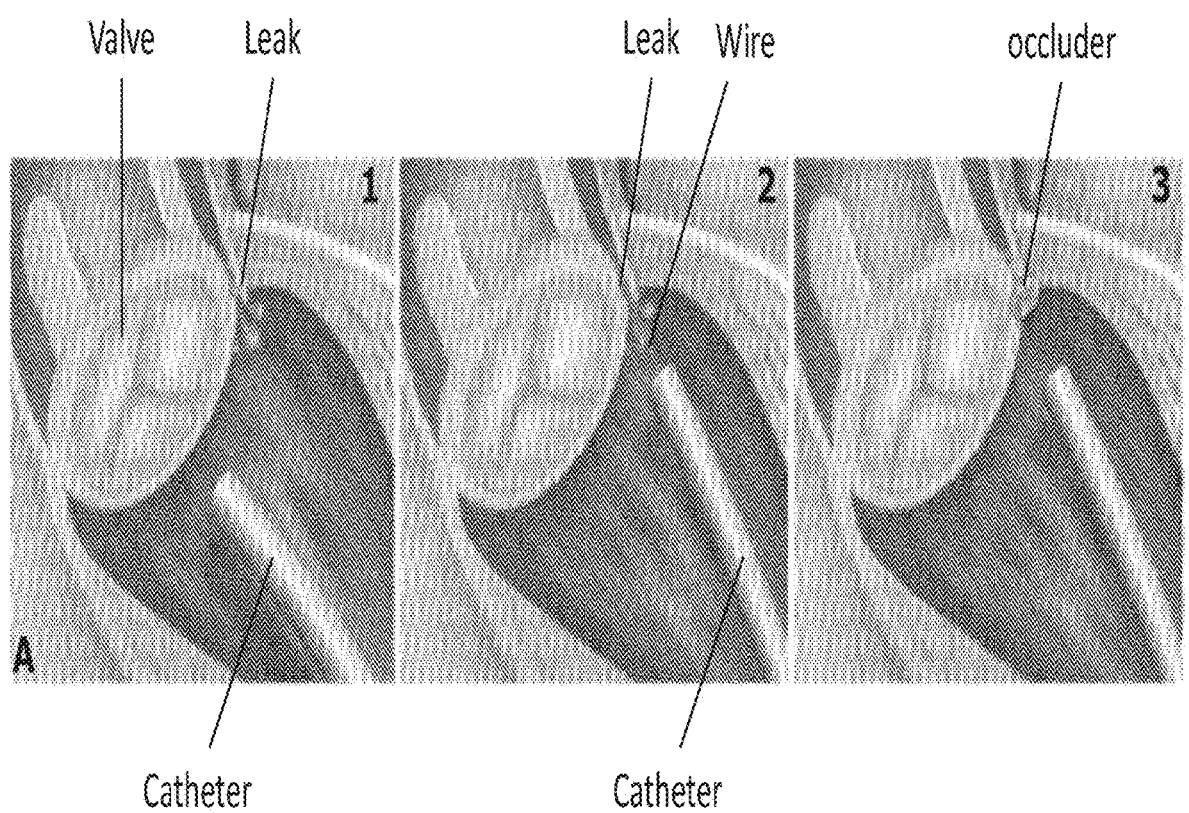
FIG. 11 illustrates a current clinical approach to paravalvular leak closure.

Paravalvular leaks occur when a gap opens between the native valve annulus and the prosthetic valve. FIG. 11 illustrates a current clinical approach to paravalvular leak closure. Transcatheter leak closure involves sequentially navigating a catheter to the leak (image 1), passing a wire from the catheter through the gap (image 2), and then deploying an expanding occluder device inside the gap (image 3). This procedure is currently manually performed using multimodal imaging (electrocardiogram-gated computed tomographic angiography, transthoracic and transesophageal echo preoperatively, and echocardiography and fluoroscopy intraoperatively), takes many hours, and requires 29.9±24.5 min of fluoroscopic x-ray exposure. Although transapical access is illustrated, approaching the valve from the aorta via transfemoral access is common.

Figure 10:
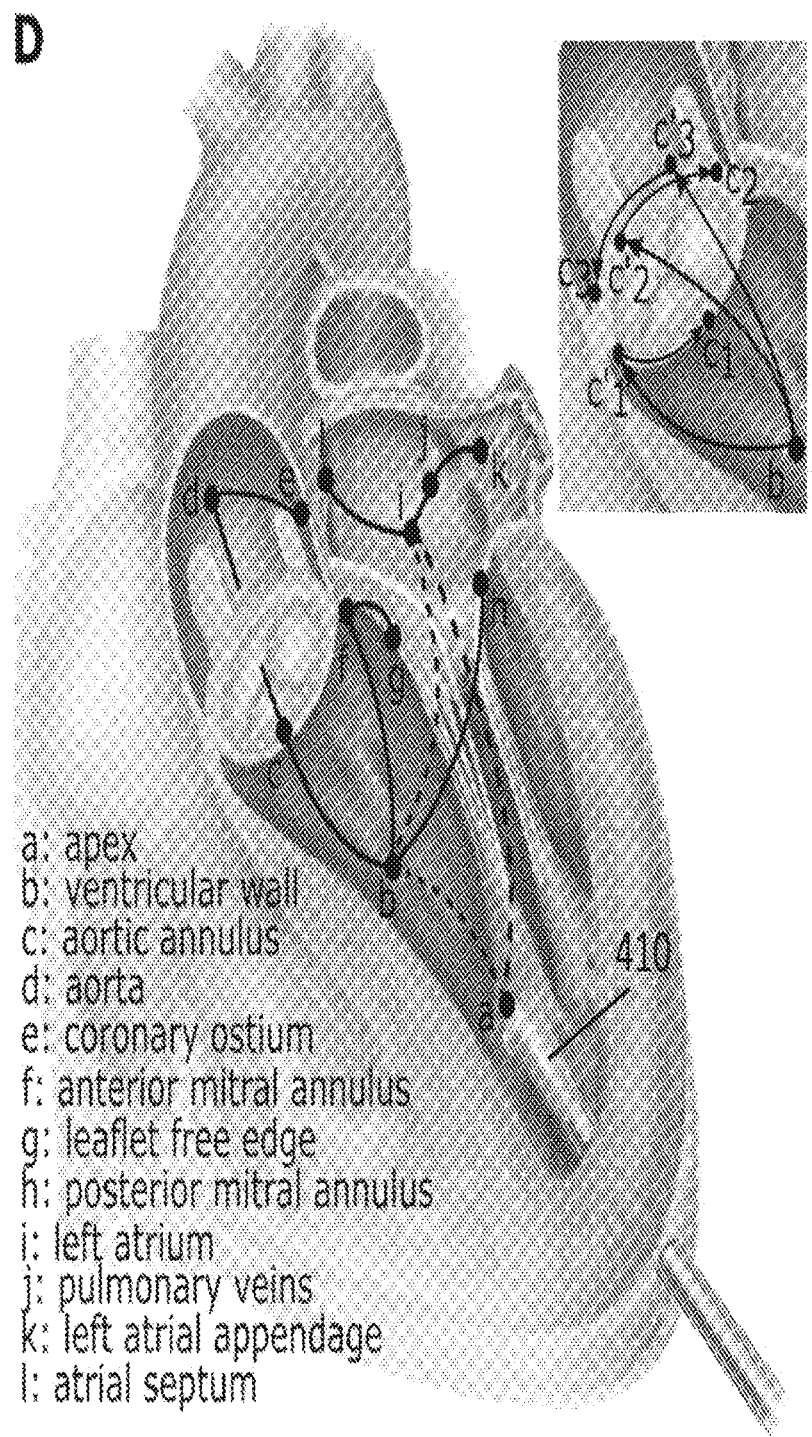
FIG. 10 illustrates the complex navigational tasks that can be achieved by following a path through a connectivity graph.

Robotic system 100 of the present disclosure may overcome these disadvantages. In particular, as shown in FIG. 10 and FIG. 3, we designed a robotic catheter for entering through the apex of the heart into the left ventricle, navigating to the aortic valve and deploying an occluder into the site of a leak. A graphical interface may display catheter tip view and geometric model of robot and valve annulus. Using leak locations determined from preoperative imaging, the catheter could either navigate autonomously to that location, or the clinician could guide it there (FIG. 3). Occluder deployment was performed under operator control.

Figure 12:
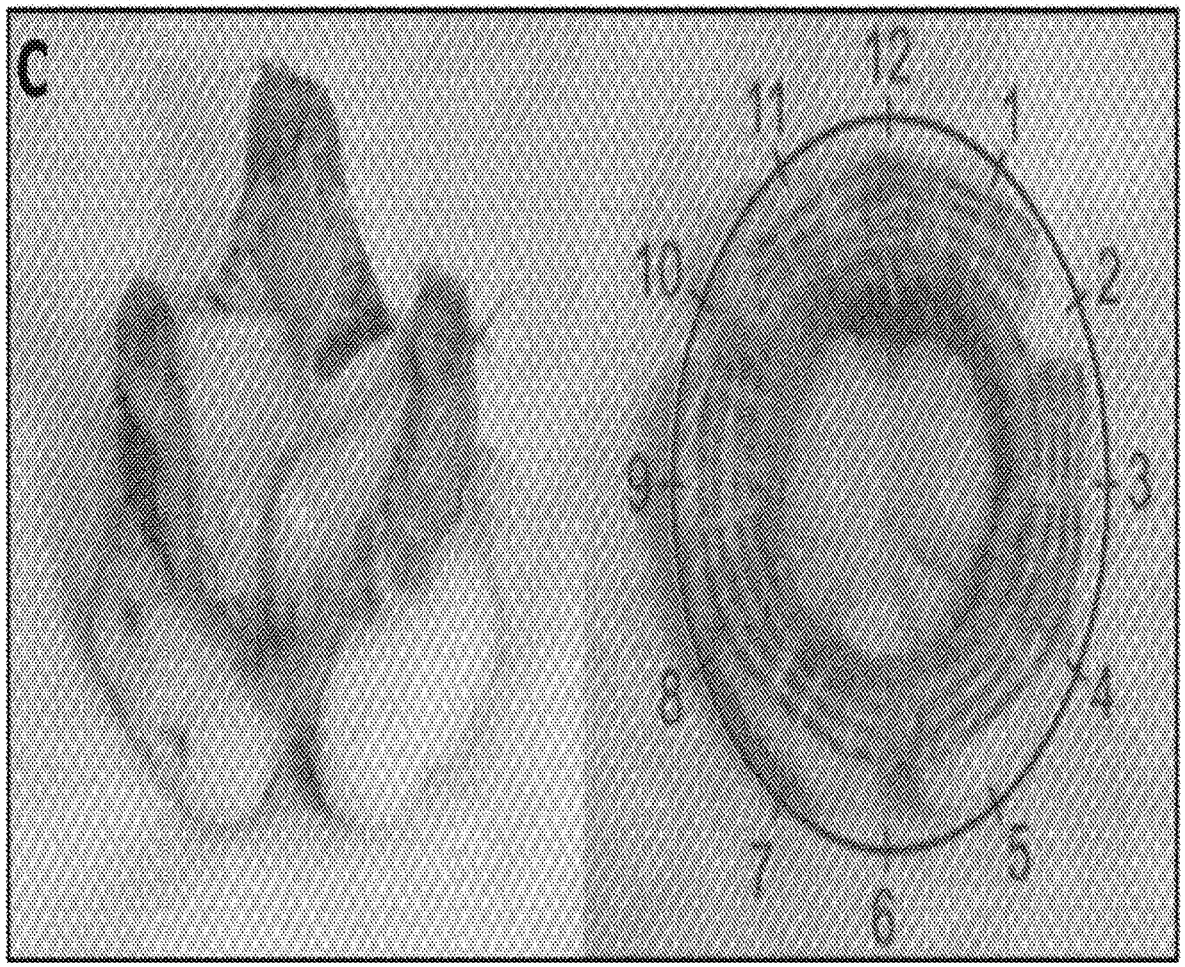
FIG. 12 depicts the valve clock coordinates.
Figure 13:
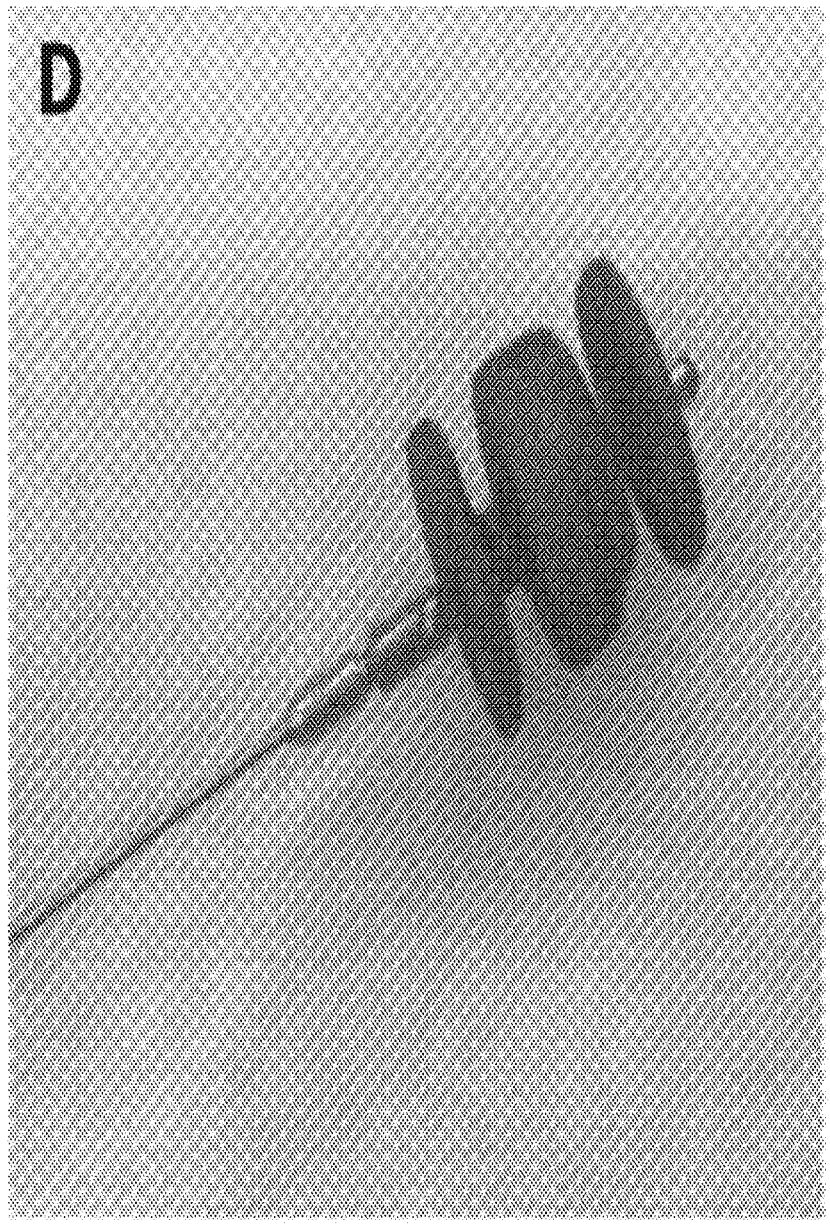
FIG. 13 depicts a vascular occluder used to plug leaks.

As shown in FIG. 12, for testing we created a porcine paravalvular leak model by replacing the native aortic valve with a bioprosthetic valve incorporating three leaks. FIG. 12 includes two views of bioprosthetic aortic valve designed to produce three paravalvular leaks at 2, 6, and 10 o'clock positions. Blue sutures are used to detect tangent to annulus. Green sutures are used to estimate valve rotation with respect to the robotic system 100. FIG. 13 shows a vascular occluder (AMPLATZER Vascular Plug II, St. Jude Medical, Saint Paul, MN) used to plug leaks.

We have implemented autonomous navigation based solely on haptic vision sensing and demonstrated the potential of the approach in the context of a challenging beating-heart procedure, aortic paravalvular leak closure. During autonomous catheter navigation to the leak location, both continuous and intermittent contact modes were used (FIG. 10). For navigation from the heart's apex to the aortic valve, the robot first located the ventricular wall (a→b) and then followed it to the aortic valve using the continuous contact mode (b→c). Because the valve annulus displaces by several centimeters over the cardiac cycle along the axis of the catheter, the robot switched to the intermittent contact mode once it detected that it had reached the aortic valve. It then navigated its tip around the perimeter of the valve annulus to the leak location specified from the preoperative imaging ($c_i' \rightarrow c_i$; FIG. 10, inset).

Switching between continuous and intermittent contact modes depends on the robot recognizing the tissue type it is touching. We implemented the capability for the catheter to distinguish the prosthetic aortic valve from blood and tissue using a machine learning classification algorithm. The classification algorithm first identified a collection of "visual words," which consisted of visual features shared between multiple images in a set of prelabeled training images, and learned the relationship between how often these visual features occurred and what the image depicted—in this case, the prosthetic valve or blood and tissue.

Navigation on the annulus of the aortic valve to the location of a leak requires two capabilities. The first is to maintain the appropriate radial distance from the center of the valve. The second is to be able to move to a specified angular location on the annulus. For robust control of radial distance, we integrated colored sutures into the bioprosthetic valve annulus that enable the navigation algorithm to compute the tangent direction of the annulus (FIG. 12). Moving to a specific angular location requires the robot to estimate its current location on the annulus, to determine the shortest path around the valve to its target location, and to detect when the target has been reached. We programmed the robot to build a geometric model of the valve as it navigates. On the basis of the estimated tangent direction of the valve annulus, as well as basic knowledge of the patient and robot position on the operating table, the robot could estimate its clock face position on the valve (FIG. 12). To account for valve rotation relative to the robot due to variability in patient anatomy and positioning, we incorporated radially oriented colored registration sutures spaced 120° apart. As the catheter navigated along the annulus and detected the registration sutures, it updated its valve model to refine the estimate of its location on the valve.

The algorithm inputs are consisted of the clock-face leak location and the desired ventricular approach direction, also specified as a clock-face position. Starting from just inside the apex of the left ventricle, the catheter moved in the desired approach direction until it detected tissue contact. It then switched to continuous contact mode and performed wall following in the direction of the valve. When the classifier detected the bioprosthetic valve in the haptic vision image, the controller switched to intermittent contact mode and computed the minimum distance direction around the annulus to the leak location based on its initial map of the annulus. As the catheter moved around the annulus in this direction, its map was refined on the basis of the detection of tangent and registration sutures. Once the leak location was reached, the robot controller acted to maintain its position at this location and sent an alert to the operator. Using joystick control, the operator could then reposition the working channel over the leak as needed, and then, the occluder could be deployed.

Evaluation and Results

FIG. 14A, FIG. 14B, FIG. 14C, and FIG. 14D depict navigation completion times from in vivo experiments. (A) Navigation from apex of the left ventricle to the aortic annulus (FIG. 10, a→b→c). (B) Circumnavigation of the entire aortic valve annulus (e.g., $c_1' \to c_1 \to c_2 \to c_3' \to c_2' \to c_3 \to c_1'$; FIG. 10, inset). (C) Navigation from apex to paravalvular leak (FIG. 10, a→b→$c_i'$→$c_i$). (D) Deployment of vascular occluder. Red bars indicate range, and dots denote outliers. P values computed as described in the "Statistical analysis" section further below.

The goal of the study was to investigate the feasibility of performing autonomous catheter navigation for a challenging intracardiac procedure in a preclinical porcine in vivo model. To perform this study, we designed and built a robotic catheter and haptic vision sensor. We also designed and wrote control algorithms, enabling the catheter to navigate either autonomously or under operator control. For our in vivo experiments, we chose transapical paravalvular leak closure as a demonstration procedure and compared autonomous and operator-controlled navigation times with each other and with previous results using a handheld catheter. For autonomous navigation, we also measured the distance between the final position of the catheter tip and the actual location of the leak.

To evaluate the autonomous navigation algorithms, we performed in vivo experiments comparing autonomous navigation with teleoperated (i.e., joystick-controlled) robotic navigation. We also compared these two forms of robotic navigation with manual navigation of a handheld catheter. In all cases, the only sensing used consisted of the video stream from the tip-mounted endoscope, kinesthetic sensing of the robot/human, and force sensing of the human (handheld). At the end of each experiment, we opened the heart, examined the ventricular walls for bruising or other tissue damage, and found none.

Figure 14A:
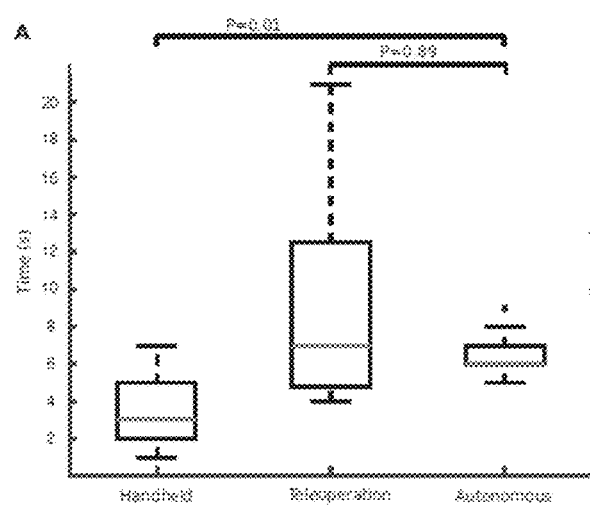
FIG. 14A, FIG. 14B, FIG. 14C, and FIG. 14D depict graphs illustrating navigation completion times from in vivo experiments.

We first compared success rate and navigation time for autonomous navigation (FIG. 10, a→b→$ci'$) from the apex of the left ventricle to the aortic annulus (five animals, 90 trials), with teleoperated control (three animals, 9 trials) and with manual control (three animals, 13 trials; FIG. 14A). Autonomous navigation consisted of first moving to a wall of the ventricle specified by clock position (FIG. 12) and then following that wall to the valve using the continuous contact control mode. Autonomous navigation was successful 99% of the time (89 of 90 trials). Autonomous control was faster than teleoperated control and with a smaller variance but slower than manual control.

Figure 14B:
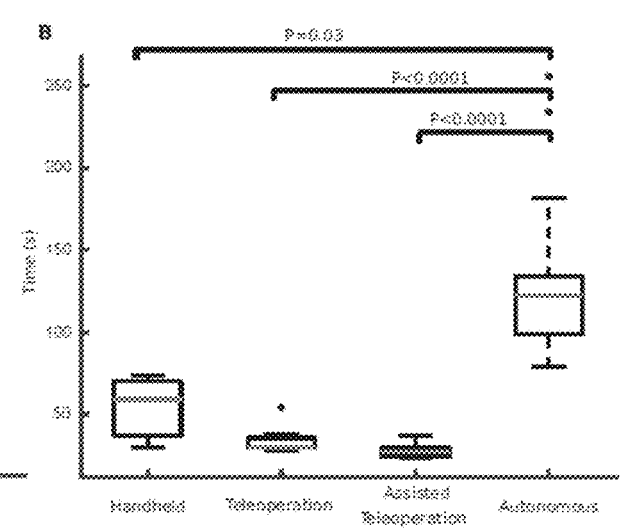
Figure 14C:
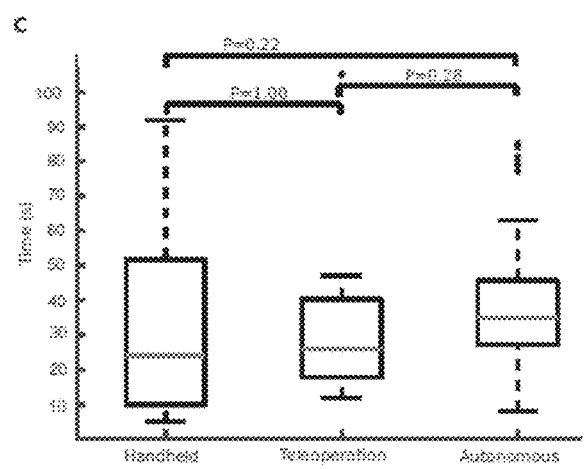

Next, we investigated the ability of the controller to navigate completely around the valve annulus using the intermittent contact mode (e.g., $c_1' \to c_1 \to c_2 \to c_3' \to c_2' \to c_3 \to c_1'$; FIG. 10, inset). This is substantially more challenging than what is required for paravalvular leak closure because, for leak closure, our algorithms enable the catheter to follow the ventricular wall in a direction that positions the catheter at an angular position on the valve that is close to the leak. For example, to reach $c_1$ in FIG. 10, the catheter could follow the path a→b→$c_1'$→$c_1$. For circumnavigation of the annulus, we compared autonomous control (three animals, 65 trials) with a handheld catheter (three animals, 3 trials) and with two forms of teleoperation (FIG. 14B). The first consisted of standard teleoperated control (one animal, 9 trials). The second corresponds to autonomous operator assistance (one animal, 10 trials). In the latter, the robot automatically controlled motion perpendicular to the plane of the valve to achieve a desired contact duty cycle, whereas the human operator manually controlled motion in the valve plane. Autonomous valve circumnavigation was successful 66% of the time (43 of 65 trials). Manual and teleoperated control had 100% success rates because the human operator, a clinician, could interpret and respond to unexpected situations. For this task, teleoperation was faster than autonomous and manual navigation, with assisted teleoperation being the fastest (FIG. 14B). Autonomous control was the slowest, taking over twice as long as manual control.

We then compared controller performance for the complete paravalvular leak navigation task (FIG. 10; a→b→ci'→ci), in which the catheter started at the heart's apex, approached the ventricular wall in a user-provided direction, moved to the aortic annulus along the ventricular wall, and then followed the annulus to the prespecified leak position (five animals, 83 trials). We chose the direction along the ventricular wall so that the catheter would arrive on the valve at a point $c_i'$, close to the leak $c_i$, but such that it would still have to pass over at least one registration marker to reach the leak. Autonomous navigation was successful in 95% of the trials (79 of 83) with a total time of 39±17 s compared with times of 34±29 s for teleoperation (three animals, 9 trials) and 31±27 s for manual navigation (three animals, 13 trials) (see FIG. 14B). Note that for teleoperated and manual navigation, the operator was not required to follow a particular path to a leak.

For autonomous navigation, we also evaluated how accurately the catheter was able to position its tip over a leak. In the first three the experiments, valve rotation with respect to the robot was estimated by an operator before autonomous operation. In the last two experiments, valve rotation was estimated by the robot based on its detection of the registration sutures. The distance between the center of the catheter tip and the center of each leak was 3.0±2.0 mm for operator-based registration (three animals, 45 trials) and 2.9±1.5 mm for autonomous estimation (two animals, 38 trials) with no statistical difference between methods (P=0.8262, Wilcoxon rank sum). This error is comparable with the accuracy to which a leak can be localized on the basis of preoperative imaging.

Figure 14D:
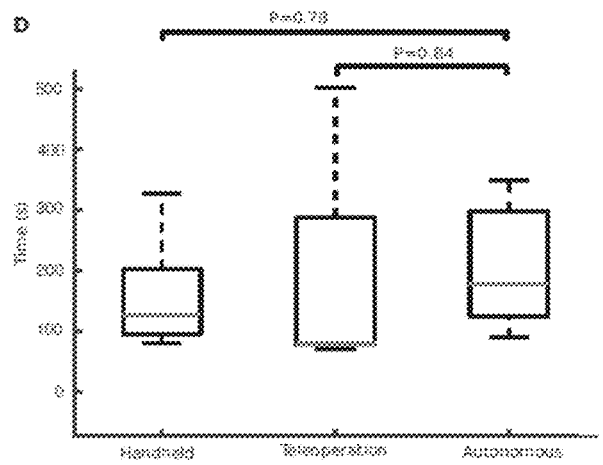

To ensure that autonomous navigation did not affect occluder delivery, we performed leak closure after autonomous, teleoperated, and manual navigation. The time to close a leak was measured from the moment either the robot or the human operator signaled that the working channel of the catheter was positioned over the leak. Any time required by the operator to subsequently adjust the location of the working channel was included in closure time (FIG. 14D). Leak closure was successful in 8 of 11 trials (autonomous navigation), 7 of 9 trials (teleoperation), and 11 of 13 trials (manual navigation). The choice of navigation method produced no statistical difference in closure success or closure time.

Figure 15:
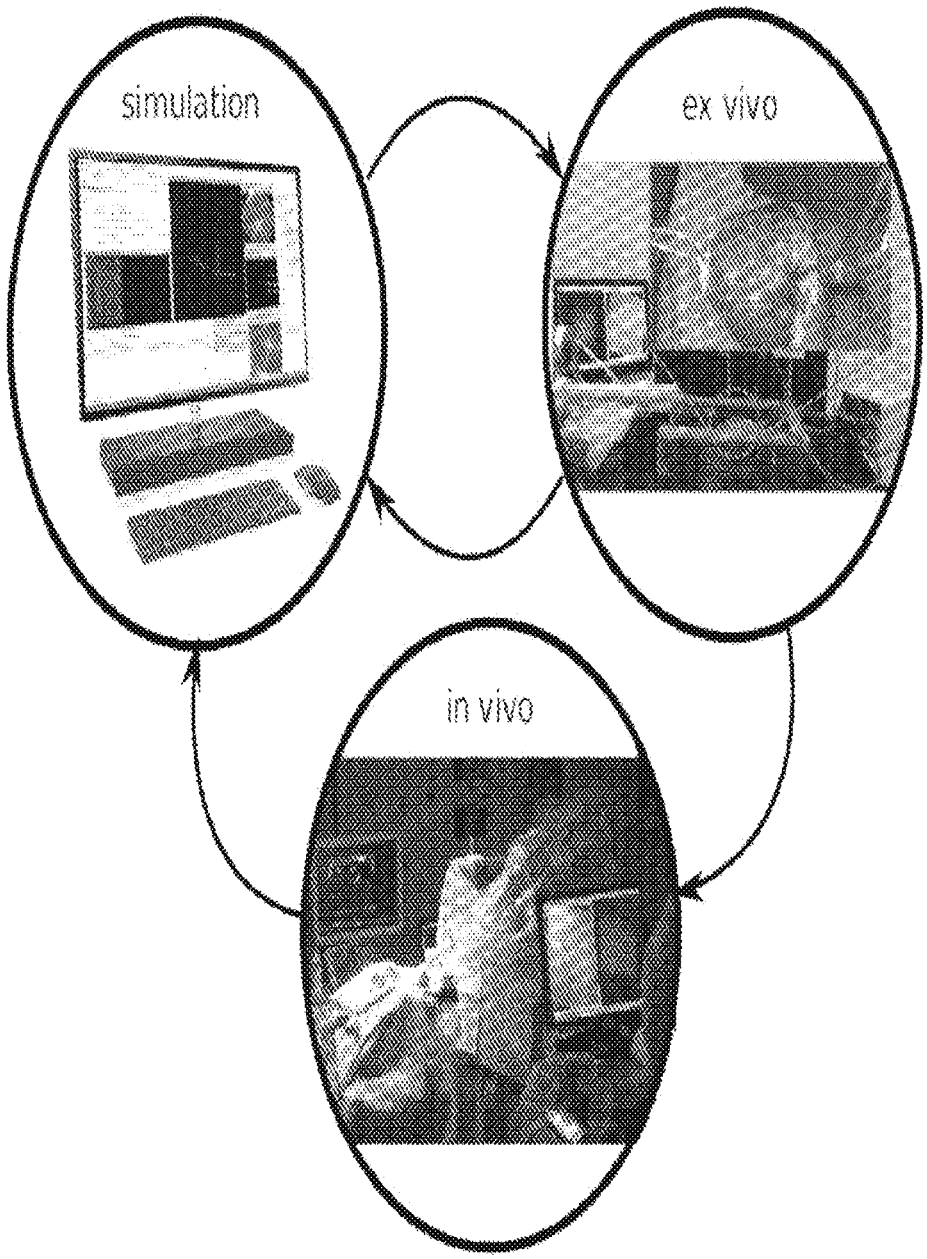
FIG. 15 illustrates a representative software development cycle.

FIG. 15 depicts a representative software development cycle. In simulation, we replayed data from previous in vivo experiments to evaluate and debug software. New features were first implemented in the simulator either to address previously identified in vivo challenges or to extend robot capabilities. New software was then tested in the ex vivo model to check the desired functionality and to ensure code stability. Identified problems were addressed by iterating between in silico and ex vivo testing. New software features were then assessed with in vivo testing. The design cycle was then completed by importing the in vivo data into the simulator and evaluating algorithm performance.

To develop and test our autonomous navigation algorithms, we implemented a development cycle composed of three steps: in silico simulation, ex vivo experiments, and in vivo experiments (FIG. 15).

We created a simulation engine that can replay timestamped data, comprising haptic vision images and robot trajectories, recorded during in vivo cases. We used the simulation engine to implement new software functionality and to troubleshoot unexpected results from in vivo experiments. After simulation, we tested new functionality on an ex vivo model comprising an explanted porcine heart, pressurized using a peristaltic pump (Masterflex Pump, 115 VAC). We immobilized the pressurized heart using sutures to attach it to a fixture. On the basis of the outcome of the ex vivo tests, we either performed additional simulations to refine the software implementation or proceeded to in vivo testing. This process was repeated iteratively for each algorithm as it was developed.

The software was executed on two PCs. One was used for catheter motion control [Intel Core Quad CPU Q9450@2.66 GHz with 4-GB random-access memory (RAM)], whereas the second was used to acquire and process images from the haptic vision sensor (Intel Core i7-6700HQ CPU@2.6 GHz with 16-GB RAM). The two computers exchanged information at runtime via transmission control protocol/internet protocol. The motion control computer received real-time heart rate data by serial port (Advisor, SurgiVet) and was also connected through universal serial bus to a six-DOF joystick (Touch, 3D Systems) that was used during teleoperated control of catheter motion. The motion control computer could execute either the autonomous navigation algorithms or the joystick motion commands. In either case, catheter tip motion commands were converted to signals sent to the motor amplifiers of the catheter drive system.

The catheter control code converting desired catheter tip displacements to the equivalent rotations and translations of the individual tubes was written in C++. The code was based on modeling the kinematics using a functional approximation (truncated Fourier series) that was calibrated offline using tip location data collected over the workspace. The calibrated functional approximation model had been previously demonstrated to predict catheter tip position more accurately (i.e., smaller average and maximum prediction error) over the workspace compared with the calibrated mechanics-based model. Catheter contact with tissue along its length produced unmodeled and unmeasured deformations that must be compensated for via tip imaging. A hierarchical control approach was used to ensure that the desired tip position was given a higher priority than the desired orientation if both criteria could not be satisfied simultaneously.

In Vivo Experiments

Interventional Procedure

We created a porcine paravalvular leak model by implanting a custom bioprosthetic device (FIG. 12) into the aortic valve position in 84.3±4.7 kg Yorkshire swine. The device was designed with three sewing ring gaps evenly distributed around its circumference (120° apart) to produce the areas of paravalvular leakage. The bioprosthetic valve consists of a titanium frame covered by a nonwoven polyester fabric. A polypropylene felt sewing ring is sutured to the frame around the annulus. Suture is passed through this ring when the valve is sewn in place inside the heart. Last, glutaraldehyde-fixed porcine pericardium leaflets are sutured to the frame.

Animal care followed procedures prescribed by the Institutional Animal Care and Use Committee. To implant the bioprosthetic valve, we premedicated the swine with atropine (0.04 mg/kg intramuscularly), followed by Telazol (4.4 mg/kg) and xylazine (2.2 mg/kg intravenously), and we accessed the thoracic cavity through a median sternotomy incision. We acquired epicardial echocardiographic images to determine the size of the valve to be implanted. Next, we initiated cardiopulmonary bypass by placing purse-string sutures for cannulation, cross-clamping the aorta, and infusing cardioplegia solution to induce asystole. We incised the aorta to expose the valve leaflets, which were then removed, and the artificial valve was implanted using nine 2-0 ETHIBOND valve sutures supra-annularly. At this point, we closed by suture the aortomy incision, started rewarming, and released the aortic cross-clamp. We maintained cardiopulmonary bypass to provide 35 to 50% of normal cardiac output to ensure hemodynamic and cardiac rhythm stability. The function of the implanted valve, as well as the leak locations and sizes, were determined by transepicardial short- and long-axis 2D and color Doppler echocardiography. Apical ventriculotomy was then performed, with previous placement of purse-string sutures to stabilize the cardiac apex for the introduction of the robotic catheter. The catheter was introduced through the apex and positioned such that its tip was not in contact with the ventricular walls. All experiments in a group were performed using the same apical catheter position. Throughout the procedure, we continuously monitored arterial blood pressure, central venous pressure, heart rate, blood oxygenation, temperature, and urine output. At the end of the experiment, a euthanasia solution was injected, and we harvested the heart for postmortem evaluation.

Autonomous Navigation from Apex to Valve

We performed experiments on five animals. For each animal, navigation was performed using three valve approach directions corresponding to 6 o'clock (posterior ventricular wall), 9 o'clock (ventricular septal wall), and 12 o'clock (anterior ventricular wall) (FIG. 12). Of the 90 total trials, the number performed in the 6, 9, and 12 o'clock directions were 31, 32, and 27, respectively.

Autonomous Circumnavigation of Aortic Valve Annulus

Experiments were performed on three animals. In the first experiment, a range of contact duty cycles was tested, whereas in the latter two experiments, the contact duty cycle was maintained between 0.3 and 0.4. In all experiments, the tangential velocity was specified as 2 mm/s during those periods when the tip was not in contact with the valve and 0 mm/s when in contact.

Autonomous Navigation from Apex to Paravalvular Leaks

We performed experiments on five animals. As an initial step for all experiments, we built a 3D spatial model of the valve by exploring the valve with the catheter under operator control. We used this model, which is separate from the model built by the autonomous controller, to monitor autonomous navigation. For three animals, we also used this model to estimate valve rotation with respect to the robot and provided this estimate as an input to the autonomous navigation algorithm. In two animals, valve rotation was estimated autonomously on the basis of the valve model built by the navigation algorithm and its detection of registration sutures.

In each experiment, navigation trials were individually performed for each of the three leaks located at 2 o'clock (n=28), 6 o'clock (n=27), and 10 o'clock (n=28) (FIG. 12). For each leak location, we selected a clock direction to follow on the ventricular wall such that the catheter would arrive at the valve annulus close to the leak but far enough away that it would have to pass over registration sutures to reach the leak. In general, this corresponded to approaching the valve at 11, 9, and 1 o'clock to reach the leaks at 2 o'clock (clock-wise), 6 o'clock (counter clockwise), and 10 o'clock (counter clockwise), respectively. If we observed that along these paths the annulus was covered by valve tissue or a suturing pledget, then we instructed the navigation algorithm to approach the leak from the opposite direction. Note that the mitral valve is located from 2 to 5 o'clock; the ventricular wall cannot be followed in these directions to reach the aortic valve. Thus, in one experiment involving operator-specified valve registration, the clockwise-approach path was covered by tissue, and we chose to approach the leak directly from the 2 o'clock direction rather than start farther away at 6 o'clock.

We designed the registration sutures to be 120° apart under the assumption to that valve rotation with respect to the robot would be less than ±60° from the nominal orientation. In one animal in which valve rotation was estimated autonomously, however, the rotation angle was equal to 60°. In this situation, it is impossible for either man or machine to determine whether the error is +60° or −60°. For these experiments, we shifted the approach direction for the leak at 6 o'clock from 9 to 8 o'clock so that the catheter would only see one set of registration sutures along the path to the leak. This ensured that it would navigate to the correct leak.

Occluder Deployment

Figure 16:
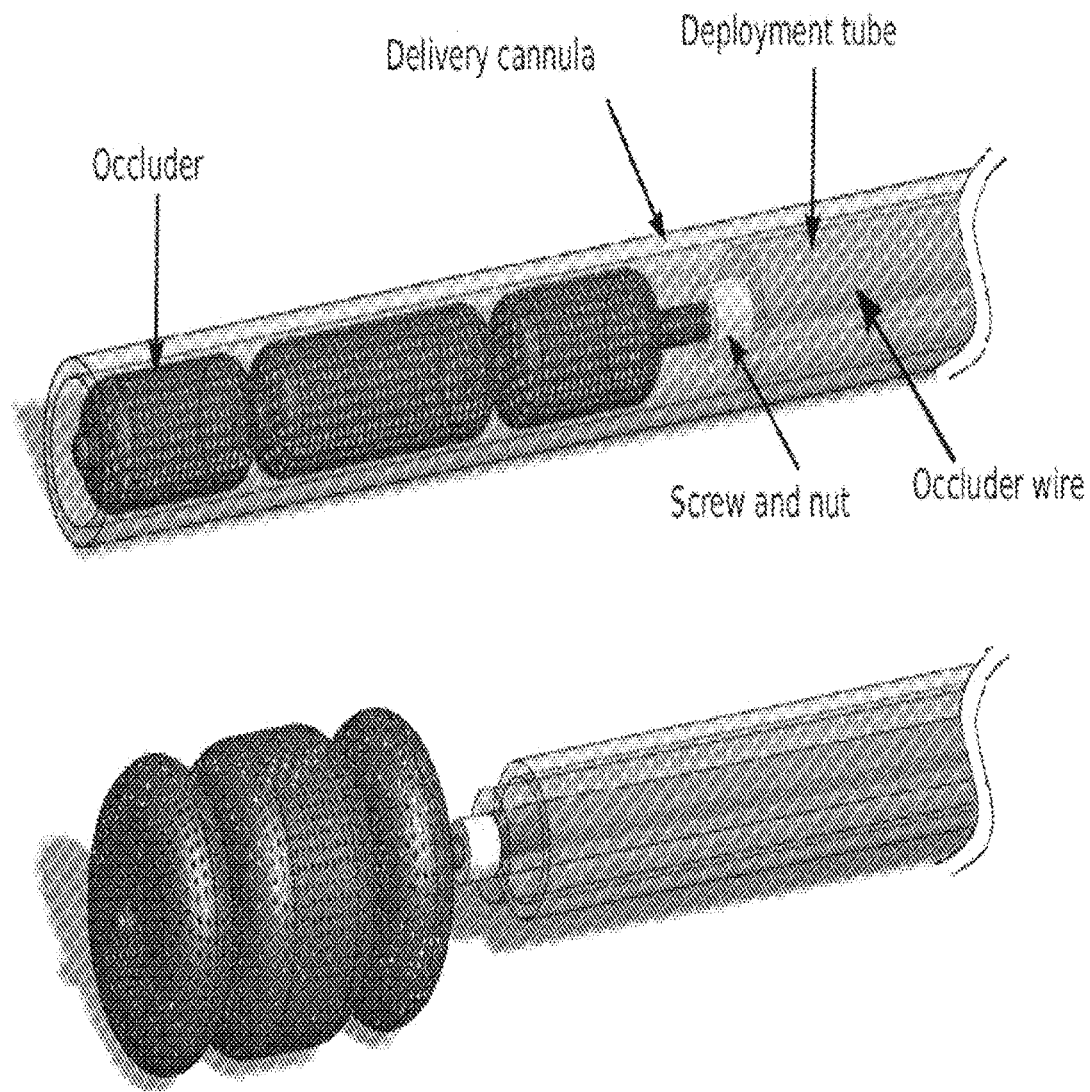
FIG. 16 depicts a representative occluder deployment system.

FIG. 16 depicts a representative occluder deployment system. The occluder, attached to a wire via a screw connection, is preloaded inside a flexible polymer delivery cannula. The delivery cannula is inserted through the lumen of the catheter into the paravalvular leak. A polymer deployment tube is used to push the occluder out of the delivery cannula. Once positioned, the occluder is released by unscrewing the wire.

After navigation to the desired leak location, the operator took control of the catheter and, as needed, centered the working channel over the leak. A three-lobed vascular occluder (AMPLATZER Vascular Plug II, AGA Medical Corporation), attached to a wire and preloaded inside a delivery cannula, was advanced ~3 mm into the leak channel (FIG. 16). The cannula was then withdrawn, allowing the occluder to expand inside the leak channel. We then retracted the wire and robotic catheter until the proximal lobe of the occluder was positioned flush with the valve annulus and surrounding tissue. If positioning was satisfactory, then the device was released by unscrewing it from the wire. If not, then the device was retracted back into the delivery cannula and the procedure was repeated as necessary.

In Vivo Calibration of Contact Duty Cycle Versus Maximum Tissue Force

Figure 17A:
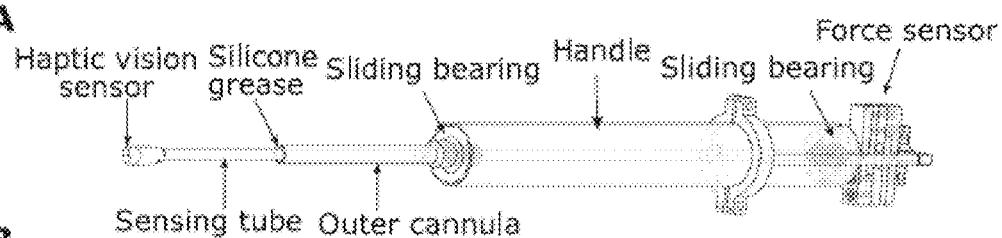
FIG. 17A illustrates a handheld instrument for the simultaneous measurement of tip contact force and contact duty cycle that combines a haptic vision sensor with a force sensor.
Figure 17B:
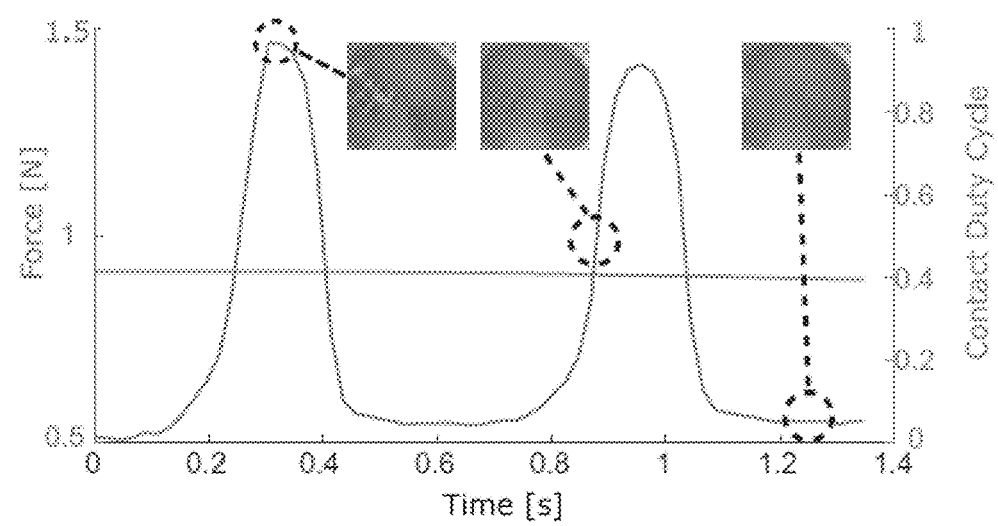
FIG. 17B shows a graph illustrating in vivo measurements of the temporal variations in contact force as a function of contact duty cycle on the aortic valve annulus.
Figure 17C:
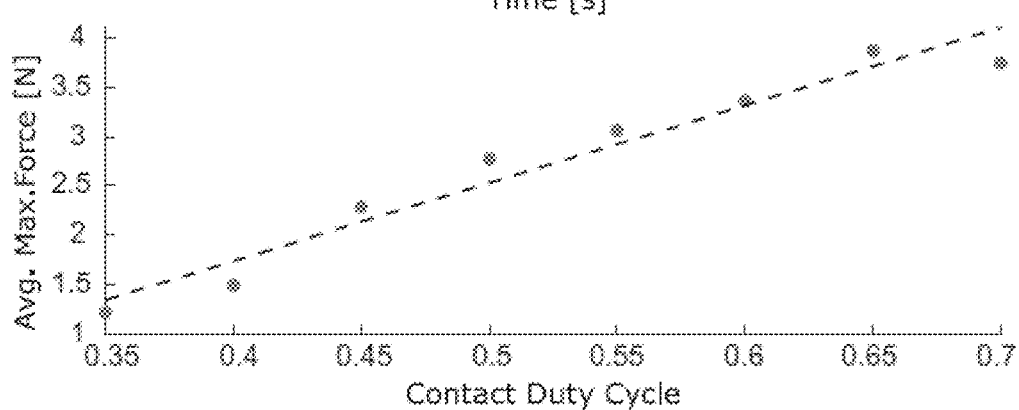
FIG. 17C shows a graph illustrating maximum contact force measurements as a function of contact duty cycle.

FIG. 17A, FIG. 17B, and FIG. 17C illustrate in vivo calibration of maximum tissue force as a function of contact duty cycle. In particular, FIG. 17A illustrates a handheld instrument for the simultaneous measurement of tip contact force and contact duty cycle that combines a haptic vision sensor with a force sensor. FIG. 17B depicts in vivo measurements of the temporal variations in contact force as a function of contact duty cycle on the aortic valve annulus. The insets show images from the haptic vision sensor at three points in the cardiac cycle. Note that the minimum force value is not necessarily zero because a small amount of tip contact with ventricular tissue can occur during systole when the valve moves away from the tip, but the ventricle contracts around it. This white (septal) ventricular tissue can be seen on the left side of the rightmost inset. FIG. 17C depicts maximum contact force measurements as a function of duty cycle. Average values of maximum force are linearly related to contact duty cycle for duty cycles in the range of 0.35 to 0.7.

To investigate the relationship between maximum contact force and contact duty cycle, we designed a handheld instrument integrating haptic vision and force sensing (FIG. 17A). The haptic vision sensor is mounted on a stiff tube that is supported by two polymer sliding bearings mounted inside the proximal handle. The proximal end of the shaft is connected to a force sensor. An outer cannula encloses the sensing shaft and extends from the handle to about 6 cm from the sensing tip. When the instrument is inserted into the apex of the heart, the outer cannula is in contact with the apical tissue, but the sensing tube is not. The gap between the outer cannula and sensing tube is filled with silicone grease to prevent blood flow from the heart into the instrument while generating minimal friction on the sensing tube. Calibration experiments indicated that the friction due to the bearings and grease was less than ±0.2 N.

We performed in vivo experiments in which we positioned the haptic vision sensor on the bioprosthetic valve annulus in locations where we could be sure that the sensor was experiencing contact only on its tip. At these locations, we collected force, heart rate, and haptic vision data (FIG. 17B). By manually adjusting instrument position along its axis, we were able to obtain data for a range of duty cycle values. The image and force data were collected at 46 Hz, and contact duty cycle based on valve contact was computed at each sampling time using a data window of width equal to the current measured cardiac period (~36 images). To remove high-frequency components not present in the force data, we then filtered the computed duty cycle using a 121-sample moving average filter corresponding to ~3.4 heartbeats. The filtered input data and the output data (e.g., FIG. 17B) were then binned using duty cycle intervals of 0.05. Last, we computed the relationship between filtered contact duty cycle and maximum applied force by averaging the maximum forces for each binned duty cycle value (FIG. 17C). We computed the Pearson's coefficient as a measure of linear relationship between the contact duty cycle and the maximum annular force. The Pearson's coefficient was equal to 0.97, which indicates a strong linear relationship. The plot of FIG. 17C indicates that the contact duty cycle range of 0.35 to 0.45 that we used in most of our experiments corresponded to a maximum force of 1.25 to 2.3 N.

Statistical Analysis

MATLAB (version R2017b) statistical subroutines were used to analyze the data and perform all statistical tests. We compared time duration for each navigation mode (i.e., handheld, teleoperated, and autonomous) for the tasks of navigating from the apex to the aortic annulus, navigating around the valve annulus, and from the apex to the leak. We also compared occluder deployment times for each navigation mode. Groups, corresponding to different navigation modes, have unequal sample sizes and sample variances. We used Levene's test to evaluate equality of variances. With no evidence of normally distributed time duration and more than two groups, we used the Kruskal-Wallis nonparametric test to check whether there are statistically significant time differences among groups. In experiments with statistical significance, we compared pairs of groups using the Mann-Whitney U test with Bonferroni correction. Data less than Q1−1.5×IQR or greater than Q3+1.5×IQR, where the interquartile range (IQR)=Q3−Q1, were considered outliers. Fisher's exact test was used to compare success rates between different groups in the case of paravalvular leak closure. Statistical significance was tested at the 5% confidence level ($P<0.05$).

Non-Contact Autonomous Navigation

In addition to or as an alternative to a force sensor, robotic system 100 may comprise a distance sensor 420 in conjunction with imaging device 411 to facilitate autonomous navigation to the interventional site. Distance sensor 420 may enable robotic system 100 to navigate to the interventional site using wall-following techniques, only without contacting (or only intermittently contacting) anatomical features, medical implants, or medical instruments along the path.

Generally speaking, distance sensor 420 may constantly or intermittently measure a distance and/or a direction between distance sensor 420 and nearby anatomical features, medical implants, or medical instruments, and the controller may utilize these distance and/or direction measurements to steer along a path that follows, but generally avoids contact with, the wall. For example, in an embodiment, the controller may be configured to steer the system so as to maintain a threshold distance from the anatomical feature, medical implant, or medical instrument. This may improve safety, navigational accuracy, and speed.

As before, in various embodiments, the controller may be configured to determine the system's location within the anatomy by processing the one or more images captured by imaging device 411 using the previously described techniques. To the extent it is necessary to displace fluid between imaging device 411 and the anatomical feature, medical implant, or medical instrument in order to capture a suitable image, in various embodiments, the controller may be configured to steer imaging device 411 toward the anatomical feature, medical device, or medical instrument and make contact therewith as previously described. Images may be captured and processed frequently enough to confirm the location of the system in the body as it is advanced to the interventional site, while distance sensor 420 steers the system to follow the wall.

Distance sensor 420, in various embodiments, may include a light-based distance sensor (e.g., those emitting laser, infrared, or other light to measure distance), a sound-based distance sensor (e.g., those emitting ultrasonic or other sound waves to measure distance), an energy-based distance sensor (e.g., radar and the like), or any other sensor suitable for measuring a distance and/or a direction between distance sensor 420 and the anatomical features, medical devices, and/or medical instruments situated a path to the interventional site.

Additionally or alternatively, in various embodiments, imaging device 410 may serve as distance sensor 420. For example, in an embodiment in which imaging device 410 includes an image sensor 411, the controller may process one or more images captured by image sensor 411 according to techniques suitable for estimating distance and/or direction based on a relative size of the anatomical feature, implanted device, or medical instrument in the image. For example, in non-contact wall-following embodiments, in which image sensor 411 captures the image at a distance, the controller may be configured to compare the relative size of the anatomical feature, implanted device, or medical instrument in the image to one or more reference images in which the distance is known, and estimate distance based on proportionality or other relational techniques (e.g., we know the implanted device is 1 cm wide and that means X image pixels=1 cm). Generally speaking, in such embodiments, the smaller the anatomical feature, implanted device, or medical instrument appears in the image, the farther away it may be from image sensor 411, and vice versa. It should be recognized that non-contact visible-spectrum image capture approaches may best be used in portions of the anatomy in which fluid is not likely to obstruct the view of image capture device 411—for example, in air-filled passages in the lungs as opposed to in blood-filled passages in the heart. Likewise, as another example, similar techniques may be used to estimate distance and/or direction in ultrasound images in embodiments in which imaging device 410 includes an ultrasonic probe. Still further, distance and/or direction could be estimated using known techniques in the art for assessing distances and/or directions from the ultrasonic probe in ultrasound imagery. For example, since scale factors in ultrasound images are generally known, the controller may be configured to utilize image processing techniques to detect a boundary of the anatomical feature, implanted device, or medical instrument and then estimate distance and/or direction based on the image. One of ordinary skill in the art will recognize other approaches suitable for estimating distance in non-contact embodiments within the scope of the present disclosure.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A robotic system, comprising:
a robotic catheter steerable by a motorized drive system;
an imaging device positioned on a distal end of the robotic catheter; and
a controller configured to:
process one or more images captured by the imaging device to identify an anatomical feature, implanted device, or medical instrument in the one or more images,
estimate a location of the imaging device in a body based on the identified anatomical feature, implanted device, or medical instrument,
determine, based on the estimated location of the imaging device, a direction in which to steer the robotic catheter for advancement towards an interventional site, and
monitor at least one of (i) a stream of images captured by the imaging device and (ii) force or distance measurements captured by the imaging device or by a sensor proximate the imaging device, to adjust the direction in which to steer the robotic catheter during advancement towards the interventional site,
wherein monitoring a stream of images captured by the imaging device to adjust the direction in which to steer the robotic catheter includes identifying whether the imaging device is contacting the anatomical feature, implanted device, or medical instrument based on whether at least a portion of an image of the stream of images is unobstructed by bodily fluid.

2. The robotic system of claim 1, wherein the robotic catheter is comprised of two or more concentric tubes.

3. The robotic system of claim 1, wherein the motorized drive system is operable to rotate and translate the robotic catheter.

4. The robotic system of claim 1, wherein the imaging device includes one of an image sensor, a camera, an ultrasonic probe, or other device configured to capture the one or more images.

5. The robotic system of claim 1, wherein the controller is configured to adjust the direction in which to steer the robotic catheter so as to maintain constant or intermittent contact with an anatomical feature during advancement towards the interventional site.

6. The robotic system of claim 1,
wherein the imaging device includes an imaging window covering the imaging device.

7. The robotic system of claim 6,
wherein the imaging window includes a surface configured to displace bodily fluid from a contact interface between the imaging window and the anatomical feature, implanted device, or medical instrument.

8. The robotic system of claim 1, wherein processing one or more images captured by the imaging device includes comparing the one or more of the captured images to representative images of one or more anatomical features, implanted devices, or medical instruments present along a pathway to a interventional site.

9. The robotic system of claim 1, wherein estimating a location of the imaging device in the body includes identifying the location of the identified anatomical feature, implanted device, or medical instrument in an anatomical model.

10. The robotic system of claim 9, wherein the anatomical model is non-dimensional.

11. The robotic system of claim 1, wherein determining the direction in which to steer the robotic catheter for advancement towards a interventional site includes determining a vector between the estimated location of the imaging device and the interventional site using an anatomical model.

12. The robotic system of claim 1, wherein monitoring a force measurement to adjust the direction in which to steer the robotic catheter includes determining whether the force measurement is substantially non-zero.

13. The robotic system of claim 1,
wherein the controller is further configured to estimate an orientation of the imaging device relative to the anatomical feature based on a distribution of a contacting surface area with respect to a center of the image.

14. The robotic system of claim 1, wherein monitoring a distance measurement to adjust the direction in which to steer the robotic catheter includes determining a distance to the anatomical feature, implanted device, or medical instrument.

15. The robotic system of claim 14, wherein the controller is configured to adjust the direction in which to steer the robotic catheter so as to avoid contact with an anatomical feature during advancement towards the interventional site.

16. A robotic system, comprising:
a robotic catheter steerable by a motorized drive system;
an imaging device positioned on a distal end of the robotic catheter; and
a controller configured to:
process one or more images captured by the imaging device to identify an anatomical feature, implanted device, or medical instrument in the one or more images,
estimate a location of the imaging device in a body based on the identified anatomical feature, implanted device, or medical instrument,
determine, based on the estimated location of the imaging device, a direction in which to steer the robotic catheter for advancement towards an interventional site, and
monitor at least one of (i) a stream of images captured by the imaging device and (ii) force or distance measurements captured by the imaging device or by a sensor proximate the imaging device, to adjust the direction in which to steer the robotic catheter during advancement towards the interventional site;
wherein the controller is further configured to estimate a contact force between the imaging device and the anatomical feature based on how much of the one or more images is unobstructed by bodily fluid.

17. The robotic system of claim 16, wherein the controller is further configured to use the estimated contact force or the force measurement to avoid generating unsafe contact forces between the imaging device and the anatomical feature, the implanted device, or the medical instrument.

18. The robotic system of claim 16, wherein the robotic catheter is comprised of two or more concentric tubes.

19. The robotic system of claim 16, wherein the motorized drive system is operable to rotate and translate the robotic catheter.

20. The robotic system of claim 16, wherein the imaging device includes one of an image sensor, a camera, an ultrasonic probe, or other device configured to capture the one or more images.

21. The robotic system of claim 16, wherein the controller is configured to adjust the direction in which to steer the robotic catheter so as to maintain constant or intermittent contact with an anatomical feature during advancement towards the interventional site.

22. The robotic system of claim 16, wherein the imaging device includes an imaging window covering the imaging device.

23. The robotic system of claim 22, wherein the imaging window includes a surface configured to displace bodily fluid from a contact interface between the imaging window and the anatomical feature, implanted device, or medical instrument.

24. The robotic system of claim 16, wherein processing one or more images captured by the imaging device includes comparing the one or more of the captured images to representative images of one or more anatomical features, implanted devices, or medical instruments present along a pathway to an interventional site.

25. The robotic system of claim 16, wherein estimating a location of the imaging device in the body includes identifying the location of the identified anatomical feature, implanted device, or medical instrument in an anatomical model.

26. The robotic system of claim 16, wherein determining the direction in which to steer the robotic catheter for advancement towards an interventional site includes determining a vector between the estimated location of the imaging device and the interventional site using an anatomical model.

27. The robotic system of claim 26, wherein the anatomical model is non-dimensional.

28. The robotic system of claim 16, wherein the controller is further configured to estimate an orientation of the imaging device relative to the anatomical feature based on a distribution of a contacting surface area with respect to a center of the image.

29. The robotic system of claim 16, wherein monitoring a force measurement to adjust the direction in which to steer the robotic catheter includes determining whether the force measurement is substantially non-zero.

30. A method for controlling a robotic system, the method comprising:
providing a robotic catheter steerable by a motorized drive system, the robotic catheter including an imaging device positioned on a distal end of the robotic catheter;
processing one or more images captured by the imaging device to identify an anatomical feature, implanted device, or medical instrument in the one or more images;
estimating a location of the imaging device in a body based on the identified anatomical feature, implanted device, or medical instrument;
determining, based on the estimated location of the imaging device, a direction in which to steer the robotic catheter for advancement towards an interventional site,
monitoring at least one of (i) a stream of images captured by the imaging device and (ii) force or distance measurements captured by the imaging device or by a sensor proximate the imaging device, to adjust the direction in which to steer the robotic catheter during advancement towards the interventional site; and
estimating a contact force between the imaging device and the anatomical feature based on how much of the one or more images is unobstructed by bodily fluid.

31. A method of controlling a robotic system, the method comprising:
providing a robotic catheter steerable by a motorized drive system, the robotic catheter including an imaging device positioned on a distal end of the robotic catheter;
processing one or more images captured by the imaging device to identify an anatomical feature, implanted device, or medical instrument in the one or more images;
estimating a location of the imaging device in a body based on the identified anatomical feature, implanted device, or medical instrument;
determining, based on the estimated location of the imaging device, a direction in which to steer the robotic catheter for advancement towards an interventional site; and
monitoring at least one of (i) a stream of images captured by the imaging device and (ii) force or distance measurements captured by the imaging device or by a sensor proximate the imaging device, to adjust the direction in which to steer the robotic catheter during advancement towards the interventional site;
wherein monitoring the stream of images captured by the imaging device to adjust the direction in which to steer the robotic catheter includes identifying whether the imaging device is contacting the anatomical feature, implanted device, or medical instrument based on whether at least a portion of an image of the stream of images is unobstructed by bodily fluid.

* * * * *